US012636158B1

(12) United States Patent
Casey et al.

(10) Patent No.: US 12,636,158 B1
(45) Date of Patent: May 26, 2026

(54) PATIENT-SPECIFIC VERTEBRAL IMPLANTS WITH POSITIONING FEATURES

(71) Applicant: Carlsmed, Inc., Carlsbad, CA (US)

(72) Inventors: Niall Patrick Casey, Carlsbad, CA (US); Gregory Mundis, La Jolla, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 19/354,023

(22) Filed: Oct. 9, 2025

Related U.S. Application Data

(63) Continuation of application No. 17/100,396, filed on Nov. 20, 2020.

(51) Int. Cl.
*A61F 2/30* (2006.01)
*A61B 34/10* (2016.01)
*A61F 2/44* (2006.01)

(52) U.S. Cl.
CPC .......... *A61F 2/30942* (2013.01); *A61B 34/10* (2016.02); *A61F 2/447* (2013.01); *A61B 2034/105* (2016.02); *A61B 2034/108* (2016.02); *A61F 2002/30952* (2013.01); *A61F 2002/30953* (2013.01)

(58) Field of Classification Search
None
See application file for complete search history.

(56) References Cited

U.S. PATENT DOCUMENTS

| | | | |
|---|---|---|---|
| 4,704,686 A | 11/1987 | Aldinger | |
| 4,936,862 A | 6/1990 | Walker et al. | |
| 5,431,562 A | 7/1995 | Andreiko et al. | |
| 5,514,180 A | 5/1996 | Heggeness et al. | |
| D420,995 S | 2/2000 | Imamura | |
| D436,580 S | 1/2001 | Navano | |
| 6,315,553 B1 | 11/2001 | Sachdeva | |
| 6,540,512 B1 | 4/2003 | Sachdeva | |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the Sonialvision safire series clinical application." medical now, No. 78; aug. 2015, 4 pages.

(Continued)

*Primary Examiner* — Nurun Flora

(74) *Attorney, Agent, or Firm* — Perkins Coie LLP

(57) ABSTRACT

The present technology provides patient-specific vertebral implants. The implants can include a cage having a geometry contoured to mate with an inferior surface of a superior vertebra and a superior surface of an inferior vertebra at a first target position. The implants can also include a plate having a geometry contoured to mate with an identified anatomical structure at a second target position. The cage and plate can be coupled in a predetermined three-dimensional orientation that simultaneously permits the cage to occupy the first target position and the plate to occupy the second target position when the implant is implanted.

20 Claims, 9 Drawing Sheets

(56)                References Cited

U.S. PATENT DOCUMENTS

| | | | |
|---|---|---|---|
| 6,696,073 | B2 | 2/2004 | Boyce et al. |
| 6,772,026 | B2 | 8/2004 | Bradbury |
| 6,932,842 | B1 | 8/2005 | Litschko et al. |
| 6,978,188 | B1 | 12/2005 | Christensen |
| 6,988,241 | B1 | 1/2006 | Guttman |
| 7,174,282 | B2 | 2/2007 | Hollister et al. |
| 7,187,790 | B2 | 3/2007 | Sabol et al. |
| D548,242 | S | 8/2007 | Viegers |
| 7,662,154 | B2 | 2/2010 | Ribeiro |
| D614,191 | S | 4/2010 | Takano |
| 7,747,305 | B2 | 6/2010 | Dean et al. |
| 7,756,314 | B2 | 7/2010 | Karau et al. |
| 7,799,077 | B2 | 9/2010 | Lang |
| D633,514 | S | 3/2011 | Tokunaga |
| D656,153 | S | 3/2012 | Imamura |
| 8,147,556 | B2 | 4/2012 | Louis et al. |
| 8,246,680 | B2 | 8/2012 | Betz |
| 8,265,949 | B2 | 9/2012 | Haddad |
| 8,273,127 | B2 | 9/2012 | Jones et al. |
| 8,275,594 | B2 | 9/2012 | Lin |
| 8,328,872 | B2 | 12/2012 | Duffield et al. |
| 8,337,507 | B2 | 12/2012 | Lang |
| 8,394,142 | B2 | 3/2013 | Bertagnoli |
| 8,454,667 | B2 | 6/2013 | Humphreys |
| 8,457,930 | B2 | 6/2013 | Shroeder |
| 8,480,716 | B2 | 7/2013 | Perrow et al. |
| 8,532,806 | B1 | 9/2013 | Masson |
| 8,556,983 | B2 | 10/2013 | Bojarski et al. |
| 8,562,655 | B2 | 10/2013 | Butler |
| 8,641,768 | B2 | 2/2014 | Duffield et al. |
| 8,644,568 | B1 | 2/2014 | Hoffman |
| 8,709,083 | B2 | 4/2014 | Duffield et al. |
| 8,735,773 | B2 | 5/2014 | Lang |
| 8,758,357 | B2 | 6/2014 | Frey |
| 8,775,133 | B2 | 7/2014 | Schroeder |
| 8,781,557 | B2 | 7/2014 | Dean |
| 8,795,373 | B2 | 8/2014 | Jones et al. |
| 8,843,229 | B2 | 9/2014 | Vanasse |
| 8,855,389 | B1 | 10/2014 | Hoffman |
| 8,858,603 | B1 | 10/2014 | Zufelt |
| 8,870,889 | B2 | 10/2014 | Frey |
| 8,932,335 | B2 | 1/2015 | Humphreys |
| 8,940,030 | B1 | 1/2015 | Stein et al. |
| 9,020,788 | B2 | 4/2015 | Lang |
| D735,231 | S | 7/2015 | Omiya |
| 9,078,718 | B2 | 7/2015 | Campbell |
| D737,309 | S | 8/2015 | Kito |
| 9,114,023 | B2 | 8/2015 | Kana et al. |
| 9,173,689 | B2 | 11/2015 | Humphreys |
| 9,198,678 | B2 | 12/2015 | Frey et al. |
| 9,208,558 | B2 | 12/2015 | Dean |
| 9,265,543 | B2 | 2/2016 | Gephart |
| 9,271,770 | B2 | 3/2016 | Costabile |
| 9,283,091 | B2 | 3/2016 | Melkent et al. |
| D757,025 | S | 5/2016 | Kim |
| 9,326,803 | B2 | 5/2016 | Humphreys |
| 9,364,340 | B2 | 6/2016 | Lawson et al. |
| 9,370,435 | B2 | 6/2016 | Walkenhorst et al. |
| D761,842 | S | 7/2016 | Johnson |
| 9,381,093 | B1 | 7/2016 | Morris et al. |
| 9,411,939 | B2 | 8/2016 | Furrer |
| 9,445,907 | B2 | 9/2016 | Meridew |
| 9,451,995 | B1 | 9/2016 | Olson |
| 9,452,050 | B2 | 9/2016 | Miles et al. |
| D774,076 | S | 12/2016 | Fuller |
| 9,532,819 | B2 | 1/2017 | Campbell |
| 9,542,525 | B2 | 1/2017 | Arisoy et al. |
| D779,065 | S | 2/2017 | Brotman et al. |
| 9,561,113 | B2 | 2/2017 | Howard |
| 9,642,633 | B2 | 5/2017 | Frey et al. |
| 9,642,652 | B2 | 5/2017 | Scioscia et al. |
| 9,675,467 | B2 | 6/2017 | Duffield et al. |
| 9,681,959 | B2 | 6/2017 | Petersheim et al. |
| 9,693,831 | B2 | 7/2017 | Mosnier et al. |
| 9,707,058 | B2 | 7/2017 | Bassett |
| 9,715,563 | B1 | 7/2017 | Schroeder |
| D797,760 | S | 9/2017 | Tsujimura |
| D797,766 | S | 9/2017 | Ibsies |
| D798,312 | S | 9/2017 | Tsujimura |
| D798,455 | S | 9/2017 | Brotman et al. |
| 9,757,163 | B2 | 9/2017 | Jacene et al. |
| 9,757,245 | B2 | 9/2017 | O'Neil et al. |
| D798,894 | S | 10/2017 | Ibsies |
| 9,775,680 | B2 | 10/2017 | Bojarski et al. |
| 9,782,228 | B2 | 10/2017 | Mosnier et al. |
| 9,848,994 | B2 | 12/2017 | Petersheim et al. |
| D812,628 | S | 3/2018 | Okado |
| 9,907,589 | B2 | 3/2018 | Ross et al. |
| 9,918,749 | B2 | 3/2018 | Altarac et al. |
| 9,918,750 | B2 | 3/2018 | Tipping et al. |
| 9,925,064 | B2 | 3/2018 | Duffield et al. |
| 9,936,984 | B2 | 4/2018 | Blain |
| 9,968,461 | B2 | 5/2018 | Zappacosta et al. |
| 9,993,341 | B2 | 6/2018 | Vanasse |
| 9,999,455 | B2 | 6/2018 | Eom |
| 10,034,676 | B2 | 7/2018 | Donner |
| 10,034,771 | B2 | 7/2018 | Capote et al. |
| D825,605 | S | 8/2018 | Jann |
| D826,977 | S | 8/2018 | Nakajima |
| 10,045,797 | B1 | 8/2018 | Walkenhorst et al. |
| 10,089,413 | B2 | 10/2018 | Wirx-Speetjens et al. |
| 10,105,238 | B2 | 10/2018 | Koch et al. |
| 10,123,884 | B2 | 11/2018 | Melkent et al. |
| 10,130,491 | B2 | 11/2018 | Garber et al. |
| 10,159,582 | B2 | 12/2018 | Gamache |
| D841,675 | S | 2/2019 | Hoffman |
| 10,213,311 | B2 | 2/2019 | Mafhouz |
| D845,973 | S | 4/2019 | Jaycobs |
| D845,974 | S | 4/2019 | Cooperman |
| D847,165 | S | 4/2019 | Kolbenheyer |
| 10,245,155 | B2 | 4/2019 | Petersheim et al. |
| D848,468 | S | 5/2019 | Ng |
| D849,029 | S | 5/2019 | Cooperman |
| D849,773 | S | 5/2019 | Jiang |
| 10,292,770 | B2 | 5/2019 | Ryan |
| 10,299,863 | B2 | 5/2019 | Grbic et al. |
| D854,560 | S | 7/2019 | Field |
| D854,561 | S | 7/2019 | Field |
| 10,390,958 | B2 | 8/2019 | Maclennan |
| D860,237 | S | 9/2019 | Li |
| D860,238 | S | 9/2019 | Bhardwaj |
| 10,405,900 | B2 | 9/2019 | Ha |
| 10,426,530 | B2 | 10/2019 | Humphreys |
| D866,577 | S | 11/2019 | Eisert |
| D867,379 | S | 11/2019 | Ang |
| D867,389 | S | 11/2019 | Jamison |
| 10,463,433 | B2 | 11/2019 | Turner et al. |
| D870,762 | S | 12/2019 | Mendoza |
| 10,492,836 | B2 | 12/2019 | Altarac et al. |
| 10,512,546 | B2 | 12/2019 | Kamer et al. |
| 10,517,681 | B2 | 12/2019 | Roh et al. |
| D872,117 | S | 1/2020 | Kobayashi |
| D872,756 | S | 1/2020 | Howell |
| 10,537,438 | B2 | 1/2020 | Martynova et al. |
| D874,490 | S | 2/2020 | Dodsworth |
| D875,761 | S | 2/2020 | Heffernan |
| D876,454 | S | 2/2020 | Knowles |
| D876,462 | S | 2/2020 | Li |
| D877,167 | S | 3/2020 | Knowles |
| D877,905 | S | 3/2020 | Linder et al. |
| D879,112 | S | 3/2020 | Hejazi |
| 10,575,960 | B2 | 3/2020 | Duffield et al. |
| 10,588,589 | B2 | 3/2020 | Bregman-Amitai et al. |
| 10,603,055 | B2 | 3/2020 | Donner et al. |
| D880,513 | S | 4/2020 | Wang |
| D881,908 | S | 4/2020 | Sunil |
| D881,910 | S | 4/2020 | Lin |
| 10,621,289 | B2 | 4/2020 | Schroeder |
| 10,631,988 | B2 | 4/2020 | Arnold et al. |
| D884,008 | S | 5/2020 | Thornberg |
| 10,646,236 | B2 | 5/2020 | Donner et al. |
| 10,646,258 | B2 | 5/2020 | Donner et al. |
| 10,729,556 | B2 | 8/2020 | Capote et al. |
| 10,736,698 | B2 | 8/2020 | Bohl |

(56)　　　　References Cited

U.S. PATENT DOCUMENTS

| | | |
|---|---|---|
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,813,773 B2 | 10/2020 | Gamache |
| 10,869,703 B2 | 12/2020 | Dunaway |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| 11,179,246 B2 | 11/2021 | Seifert et al. |
| 11,185,369 B2 | 11/2021 | Ryan |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| 11,259,937 B2 | 3/2022 | Shi et al. |
| 11,304,820 B2 | 4/2022 | Terrell et al. |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| D971,411 S | 11/2022 | Kang et al. |
| 11,504,175 B2 | 11/2022 | Bush et al. |
| 11,510,708 B2 | 11/2022 | Lewis et al. |
| 11,547,457 B2 | 1/2023 | Cordaro et al. |
| 11,547,459 B2 | 1/2023 | Ahn |
| D979,063 S | 2/2023 | Refai |
| 11,612,492 B2 | 3/2023 | McDonough et al. |
| 11,633,290 B2 | 4/2023 | Valkoun et al. |
| D1,004,776 S | 11/2023 | James |
| 11,813,006 B2 | 11/2023 | Lauf et al. |
| 12,053,212 B2 | 8/2024 | Afshar et al. |
| 12,232,980 B2 | 2/2025 | Cordonnier |
| 12,245,952 B2 | 3/2025 | Casey et al. |
| 12,251,320 B2 | 3/2025 | Casey et al. |
| 12,324,746 B2 | 6/2025 | Shin |
| 2002/0016595 A1 | 2/2002 | Michelson |
| 2004/0104512 A1 | 6/2004 | Eidenschink |
| 2004/0210314 A1 | 10/2004 | Michelson |
| 2005/0049590 A1 | 3/2005 | Alleyne et al. |
| 2007/0276501 A1 | 11/2007 | Betz |
| 2008/0089566 A1 | 4/2008 | Node-Langlois |
| 2008/0227047 A1 | 9/2008 | Lowe |
| 2009/0062739 A1 | 3/2009 | Anderson |
| 2010/0298942 A1 | 11/2010 | Hansell |
| 2010/0324692 A1 | 12/2010 | Uthgenannt |
| 2012/0150243 A9 | 6/2012 | Crawford et al. |
| 2012/0322018 A1 | 12/2012 | Lowe |
| 2013/0079680 A1 | 3/2013 | Stein et al. |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0164022 A1 | 6/2014 | Reed |
| 2014/0263674 A1 | 9/2014 | Cerveny |
| 2014/0277487 A1 | 9/2014 | Davenport et al. |
| 2014/0350614 A1 | 11/2014 | Frey |
| 2015/0079533 A1 | 3/2015 | Lowe |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0328005 A1 | 11/2015 | Padovani et al. |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354161 A1 | 12/2016 | Deitz |
| 2016/0354213 A1 | 12/2016 | Cowan |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0061375 A1 | 3/2017 | Laster |
| 2017/0068792 A1 | 3/2017 | Reiner |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0250075 A1 | 9/2018 | Cho |
| 2018/0271602 A1 | 9/2018 | Frey et al. |
| 2018/0301213 A1 | 10/2018 | Zehavi et al. |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0318100 A1 | 11/2018 | Altarac |
| 2018/0338841 A1 | 11/2018 | Miller et al. |
| 2019/0029842 A1 | 1/2019 | Xiao et al. |
| 2019/0065685 A1 | 2/2019 | Pickover |
| 2019/0105170 A1 | 4/2019 | Wang et al. |
| 2019/0133783 A1 | 5/2019 | Unger et al. |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2020/0021570 A1 | 1/2020 | Lin |
| 2020/0046511 A1 | 2/2020 | Singh et al. |
| 2020/0078180 A1 | 3/2020 | Casey et al. |
| 2020/0085509 A1 | 3/2020 | Roh et al. |
| 2020/0170802 A1 | 6/2020 | Casey et al. |
| 2020/0246162 A1 | 8/2020 | Schultz et al. |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2020/0323654 A1 | 10/2020 | Marrapode |

(56) References Cited

U.S. PATENT DOCUMENTS

| | | |
|---|---|---|
| 2021/0015524 A1 | 1/2021 | Montello et al. |
| 2021/0059822 A1 | 3/2021 | Casey et al. |
| 2021/0064605 A1 | 3/2021 | Balint |
| 2021/0068975 A1 | 3/2021 | Choi et al. |
| 2021/0085482 A1 | 3/2021 | Flickinger et al. |
| 2021/0145519 A1 | 5/2021 | Mosnier et al. |
| 2021/0209757 A1 | 7/2021 | Min et al. |
| 2021/0210189 A1 | 7/2021 | Casey et al. |
| 2021/0287770 A1 | 9/2021 | Anderson |
| 2021/0382457 A1 | 12/2021 | Roh et al. |
| 2022/0000625 A1 | 1/2022 | Cordonnier |
| 2022/0006642 A1 | 1/2022 | Maj et al. |
| 2022/0015918 A1 | 1/2022 | Parr et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1* | 5/2022 | Casey ............... G16H 50/20 |
| 2022/0401150 A1 | 12/2022 | Cordonnier |
| 2023/0052263 A1 | 2/2023 | Casey et al. |
| 2023/0372122 A1 | 11/2023 | Martin et al. |
| 2024/0225705 A1 | 7/2024 | Flint et al. |
| 2024/0350179 A1 | 10/2024 | Wolfe et al. |
| 2024/0374395 A1 | 11/2024 | Padovani et al. |
| 2025/0072946 A1 | 3/2025 | Blain et al. |
| 2025/0127626 A1 | 4/2025 | Walters et al. |

FOREIGN PATENT DOCUMENTS

| | | |
|---|---|---|
| CN | 204468348 U | 7/2015 |
| CN | 105796214 A | 7/2016 |
| CN | 106202861 A | 12/2016 |
| CN | 107220933 B | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 A | 11/2021 |
| EP | 3120796 A1 | 1/2017 |
| WO | WO9507509 A1 | 3/1995 |
| WO | WO2004110309 A2 | 12/2004 |
| WO | WO2010151564 A1 | 12/2010 |
| WO | WO2012154534 A1 | 11/2012 |
| WO | WO2014180972 A2 | 11/2014 |
| WO | WO2016172694 A1 | 10/2016 |
| WO | WO2019018013 A1 | 1/2019 |
| WO | WO2019112917 A1 | 6/2019 |
| WO | WO2019148154 A1 | 8/2019 |
| WO | WO2019165152 A1 | 8/2019 |
| WO | WO2019241167 A1 | 12/2019 |
| WO | WO2021061662 A1 | 4/2021 |
| WO | WO2022045956 A1 | 3/2022 |
| WO | WO2022109097 A1 | 5/2022 |
| WO | WO2022261171 A1 | 12/2022 |
| WO | WO2022266313 A1 | 12/2022 |
| WO | WO2023034405 A1 | 3/2023 |
| WO | WO2025023347 A1 | 1/2025 |
| WO | WO2025085702 A1 | 4/2025 |

OTHER PUBLICATIONS

International Search Report and Written Opinion for International Patent Application No. PCT/US21/59837, mailed Feb. 7, 2022, 19 pages.
Materialise Mimics, "Efficiently turn scans into accurate virtual 3D models," Retrieved on Nov. 1, 2019 at www.materialize.com/en/medical/software/mimics, 1 page.
Pimenta, Dr. Luiz, "Current Surgical Strategies to Restore Proper Sagittal Alignment," Journal of Spine 2015, vol. 4, Issue 4, 2 pages.

* cited by examiner

600

Provide patient-specific implant having a cage and a plate — 602

Couple the plate to the cage — 604

Deliver implant to target region proximate patient's spine — 606

Position plate at second target position — 608

Confirm cage is positioned at first target position — 610

700

Provide patient-specific
implant having a cage and a
plate — 702

Deliver cage to location
proximate the first target
position — 704

Deliver plate to location
proximate the second
target position — 706

Position plate at second
target position — 708

Couple plate to cage — 710

Confirm cage is positioned
at first target position — 712

1

PATIENT-SPECIFIC VERTEBRAL IMPLANTS WITH POSITIONING FEATURES

TECHNICAL FIELD

The present disclosure is generally related to orthopedic implants, and more particularly to systems and methods for designing and implementing patient-specific orthopedic implants.

BACKGROUND

Orthopedic implants are used to correct numerous different maladies in a variety of contexts, including spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. Spine surgery itself may encompass a variety of procedures and targets, such as one or more of the cervical spine, thoracic spine, lumbar spine, or sacrum, and may be performed to treat a deformity or degeneration of the spine and/or related back pain, leg pain, or other body pain. Common spinal deformities that may be treated using an orthopedic implant include irregular spinal curvature such as scoliosis, lordosis, or kyphosis (hyper- or hypo-), and irregular spinal displacement (e.g., spondylolisthesis). Other spinal disorders that can be treated using an orthopedic implant include osteoarthritis, lumbar degenerative disc disease or cervical degenerative disc disease, lumbar spinal stenosis, and cervical spinal stenosis.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Non-limiting and non-exhaustive descriptions are described with reference to the following drawings. The components in the figures are not necessarily to scale, emphasis instead being placed upon illustrating principles.

2

Figure 4:
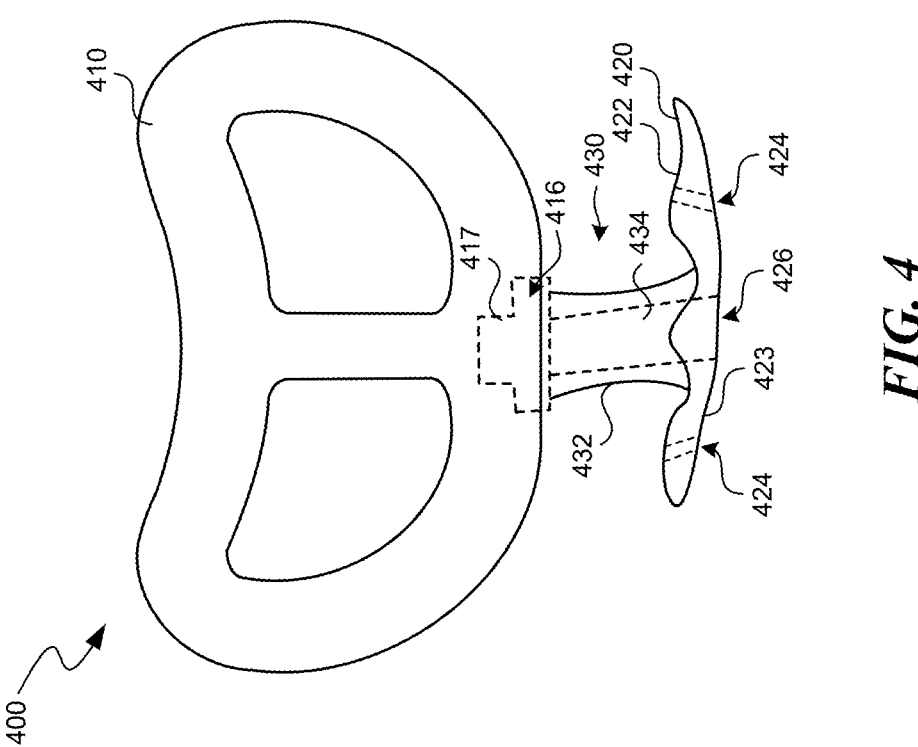

FIG. 4 is a partially schematic top view of a patient-specific implant with an interlocking cage and plate and configured in accordance with embodiments of the present technology.

Figure 5:
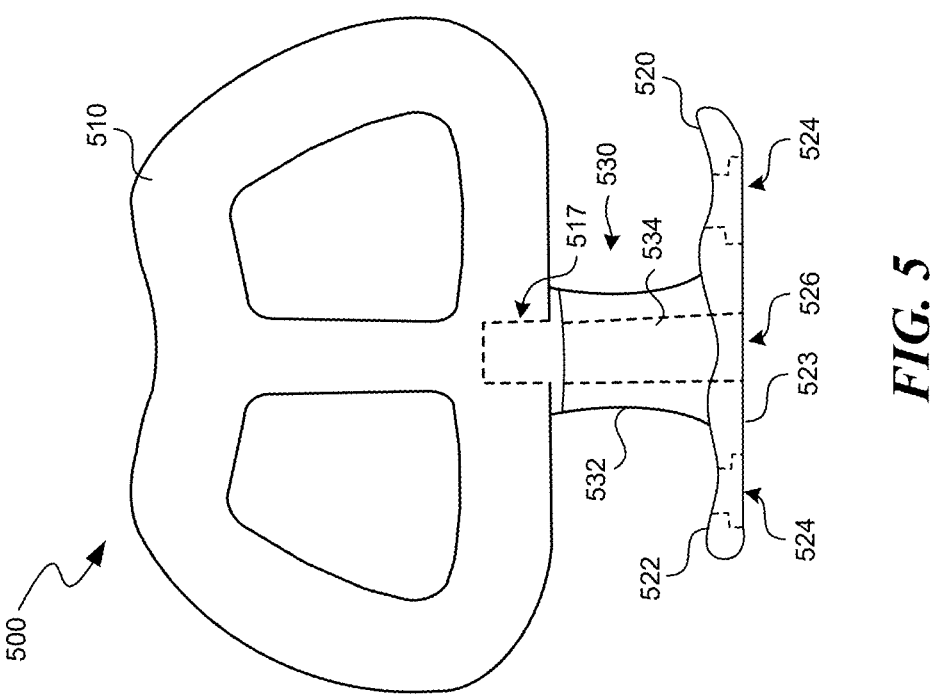

FIG. 5 is a partially schematic top view of another patient-specific implant with an interlocking cage and plate and configured in accordance with embodiments of the present technology.

Figure 6:
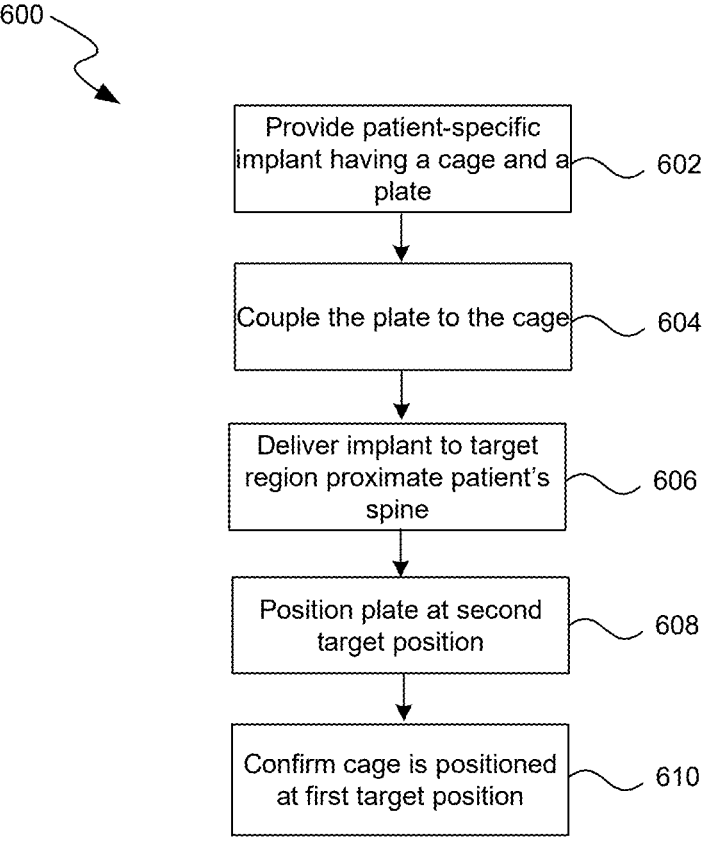

FIG. 6 is a flowchart of a method for implanting a patient-specific implant to a target position in a patient's spinal column in accordance with embodiments of the present technology.

Figure 7:
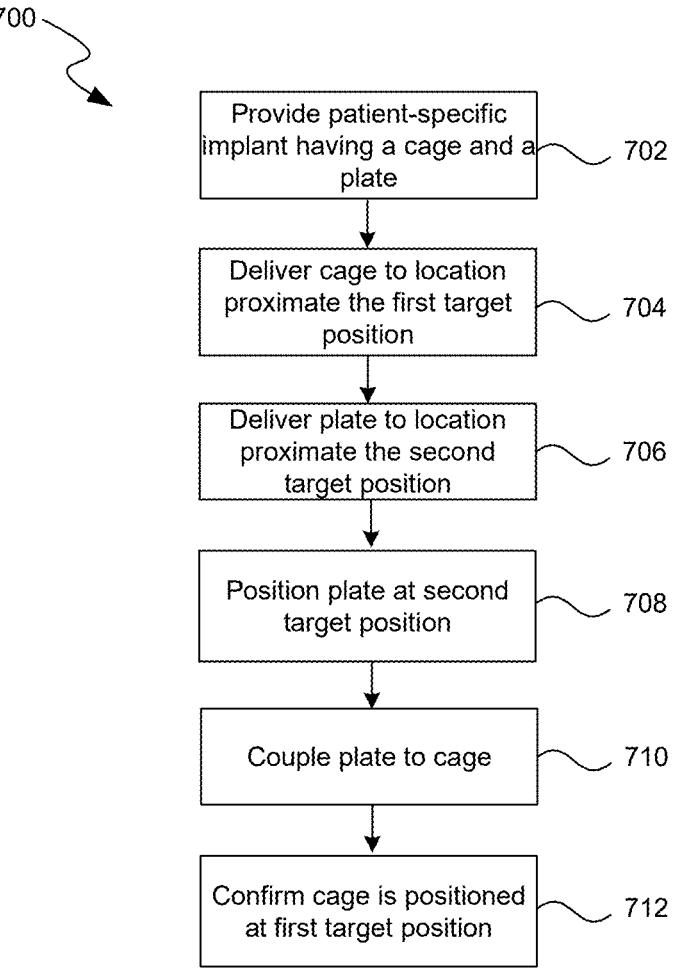

FIG. 7 is a flowchart of another method for implanting a patient-specific implant to a target position in a patient's spinal column in accordance with embodiments of the present technology.

Figure 8:
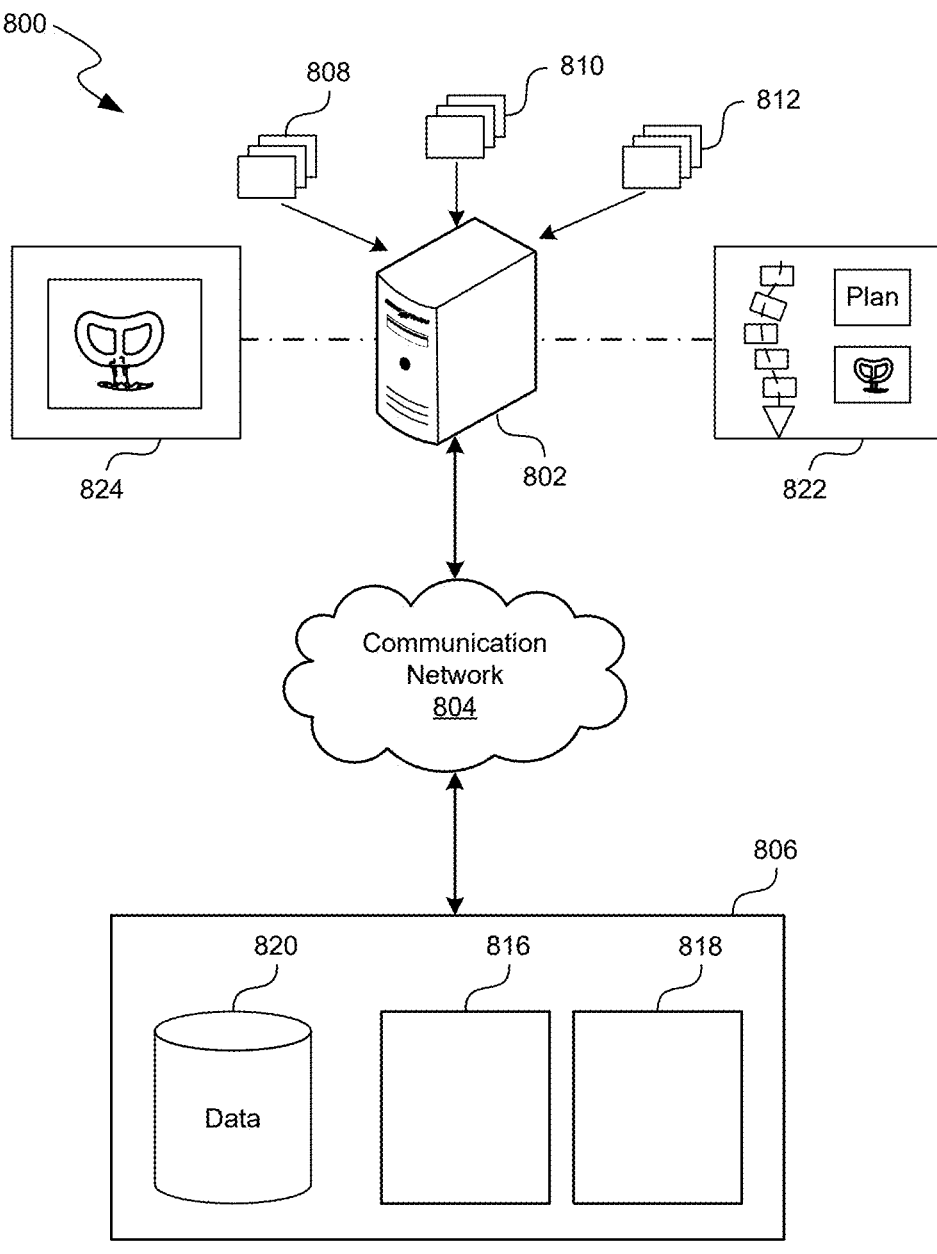

FIG. 8 is a network connection diagram illustrating a system for providing patient-specific medical care and configured in accordance with select embodiments of the present technology.

Figure 9:
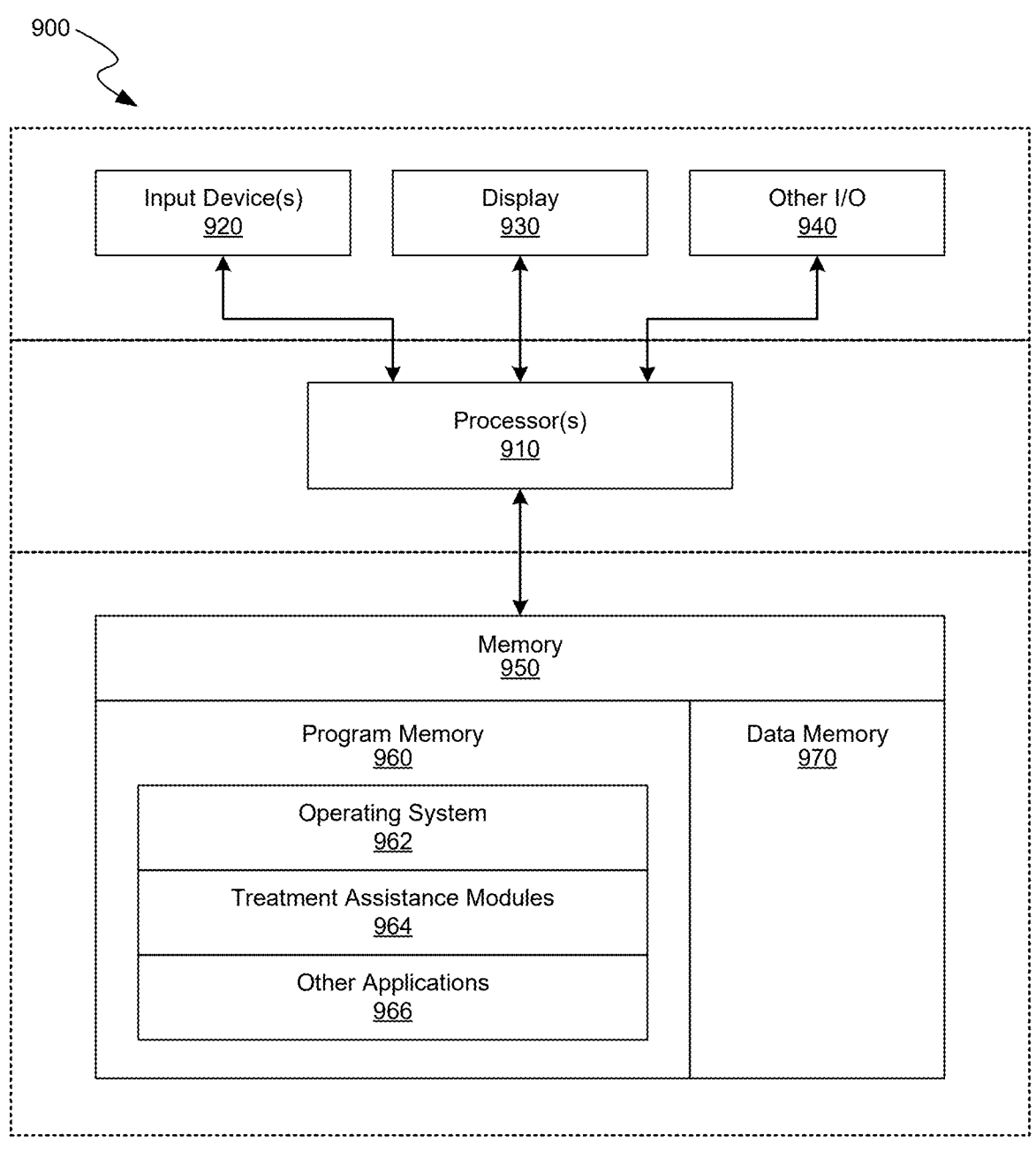

FIG. 9 illustrates a computing device suitable for use in connection with the system of FIG. 8, in accordance with select embodiments of the present technology.

Figure 10:
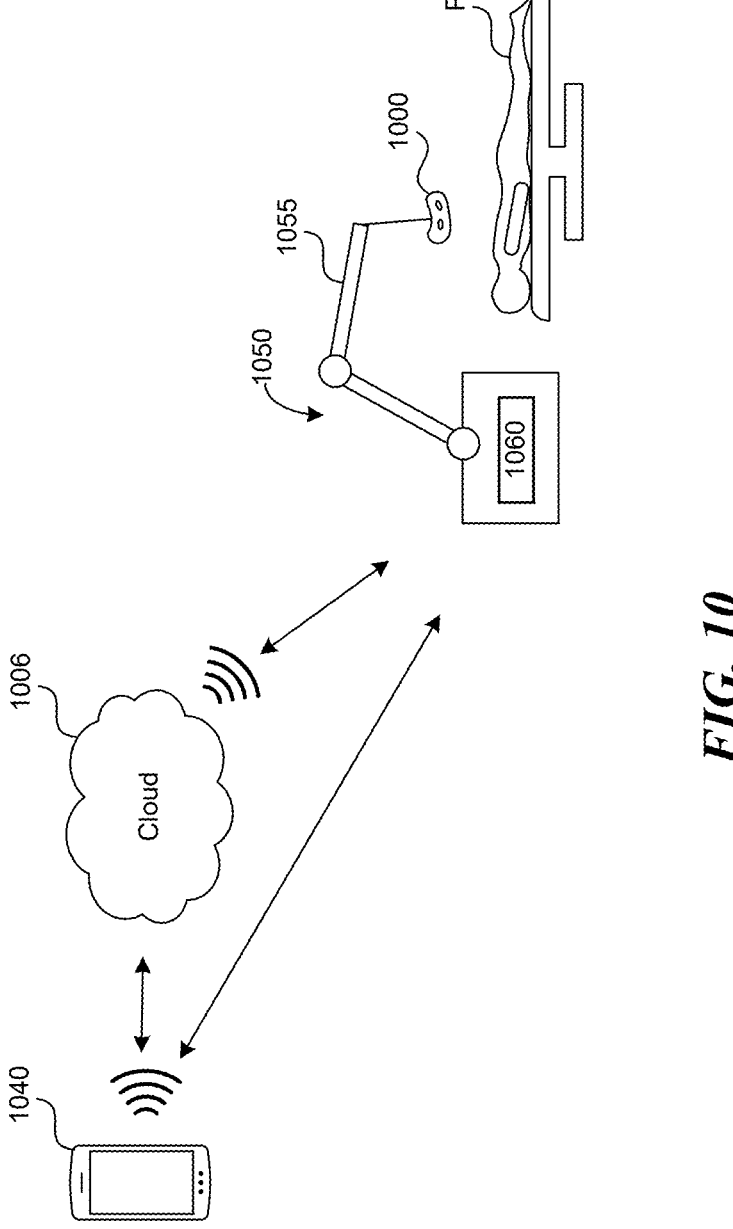

FIG. 10 is a partially schematic illustration of an operative setup for implanting a patient-specific implant into a patient, in accordance with embodiments of the present technology.

DETAILED DESCRIPTION

I. Overview of Technology

The present technology is directed to patient-specific medical device implants that are designed based on a patient's anatomy. For example, in many of the embodiments disclosed herein, the present technology provides patient-specific vertebral implants designed to be implanted between two vertebral bodies. The vertebral implants can include both a patient-specific interbody device (e.g., a cage) and a patient-specific positioning feature. The interbody device can be designed to occupy a first target position between the two vertebral bodies. The positioning feature can be designed to occupy a second target position proximate at least one of the two vertebral bodies. The positioning feature can be a plate, and the plate and the interbody device can be mechanically coupled together by a connection mechanism. The connection mechanism can be designed to connect the interbody device to the plate to form a predetermined three-dimensional spatial relationship therebetween that simultaneously permits the cage to occupy the first target position and the plate to occupy the second target position. Because the plate and the interbody device are in a predetermined three-dimensional spatial relationship when coupled together, a surgeon implanting the implant need only confirm that either the plate is in the second target position or the interbody device is in the first target position. If, for example, the surgeon confirms the plate is in the second target position, the interbody device will be in the first target position by virtue of the predetermined spatial relationship between the interbody device and the plate.

The present technology further provides methods for implanting the patient-specific implants. For example, in some embodiments, the interbody device and plate can be implanted in an uncoupled state. In such embodiments, the interbody device can be delivered proximate the first target position. The plate can then be delivered to the second target position. Once the plate is in the second target position, the plate can be coupled to the interbody device. The act of coupling the plate to the interbody device can move the interbody device into the first target position. The plate can be configured to match the geometry of anatomical features against which it rests. For example, the plate can have a curved surface that is generally geometrically congruent to a region of the outer surface of the vertebral body. When the plate pressed against the region, the matching surfaces can engage one another to key the plate to the vertebral body. Accordingly, the patient specific configuration of the plate can be used to position and align the plate with the spine. In some embodiments, the interbody device and plate can be delivered in a coupled state. Regardless of whether the interbody device and the plate are delivered in a coupled or uncoupled state, the mechanical coupling between the interbody device and the plate can provides a desired orientation and positioning between the interbody device and the plate such that when the plate is in the second target position, the interbody device is in the first target position, and vice versa. Once implanted, the plate can also prevent and/or reduce movement (e.g., expulsion, migration, etc.) of the interbody device.

Without being bound by theory, intervertebral implants provide the most efficacy when they are implanted at the correct position. This is especially true for "patient-specific" intervertebral implants, which, as described in detail below, are designed to mate with specific anatomical targets. However, depending on the surgical approach and the type of device being implanted, it can be difficult to deliver intervertebral implants (e.g., interbody devices such as cages) to precise target locations in an intervertebral disc space. For example, because the disc space is between two vertebral bodies, the precise target location often cannot be directly seen and/or accessed by the surgeon performing the implant procedure. The target location is also typically at the bottom of a narrow surgical corridor that can further reduce the ability of a surgeon to see the target site and/or reduce maneuverability of the implant once proximate the target site. The present technology thus provides systems, devices, and associated methods that direct the intervertebral implants into the target position without having to directly visualize the target size. Without being bound by theory, the present technology is therefore expected to improve the accuracy with which interbody devices can be delivered to relatively "difficult to visualize" target positions, such as intervertebral disc spaces.

The plates described herein can therefore have at least two functions: ensuring the interbody device is positioned at the correct (and relatively difficult-to-visualize) target position and reducing movement of the interbody device once it is located at the target position. The plates can be designed to mate with a portion of patient anatomy at a second target position that is relatively easier to visualize and/or access than the interbody target position. For example, the plates can be designed to mate with one or more surfaces of the vertebral body (e.g., an anterior surface of a vertebral body, a lateral surface of a vertebral body, etc.). The plates can also be coupled to the interbody device to form a predefined three-dimensional spatial relationship therebetween. For example, when the plate is coupled to the interbody device, the interbody device can have a predefined position, orientation, alignment, and/or geometry relative to the plate. The predefined three-dimensional orientation can thus be designed to ensure that, when the plate is positioned at the relatively easier to visualize plate target position, the interbody device is directed into the relatively harder to visualize interbody target position. Thus, the plate can be used to help guide the interbody device into position. The plate can be mechanically coupled to the spine by one or more fasteners (e.g., bone screws, anchors, etc.). The fasteners can further prevent or limit movement of the plate relative to the adjacent vertebrae.

In some embodiments, a patient-specific intervertebral implant includes an intervertebral cage configured to mate with endplates of adjacent vertebral bodies, a patient-specific positioning feature configured to mate with a target region of at least one of the adjacent vertebral bodies, and a connection mechanism. The connection mechanism can couple or be configured to couple the patient-specific positioning feature to the intervertebral cage to maintain a predetermined configuration of the patient-specific intervertebral implant when the intervertebral cage is between the endplates and the patient-specific positioning feature contacts the target region. The predetermined configuration can correspond to a target spatial relationship between the cage and positioning feature.

The present technology thus provides systems and methods for designing and implanting "patient-specific" or "personalized" medical devices, that are expected to mitigate at least some of the disadvantages of conventional intervertebral implants. In particular, the present technology provides systems and methods for designing and implanting patient-specific implants that are optimized for the patient's particular characteristics (e.g., condition, anatomy, pathology, medical history, etc.). For example, the patient-specific medical device can be designed and manufactured specifically for the particular patient, rather than being an off-the-shelf device. However, it shall be appreciated that a patient-specific or personalized medical device can include one or more components that are non-patient-specific, and/or can be used with an instrument or tool that is non-patient-specific. For example, patient-specific positioning features can be used with non-patient-specific articulating intervertebral implants, fixed intervertebral implants, cages, etc. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof. The implants can include positioning features selected based on the implantation site, delivery paths, or the like. Positioning features can be or include, for example, plates, plate assemblies (e.g., plates and one or more fasteners, plates with locators, etc.), arms (e.g., deployable or nondeployed arms), or combinations thereof. For example, an implant can have arms that are deployed to contact specific positions along the spinal column.

In some embodiments, the patient-specific implants described herein are designed to occupy a specific target position once implanted. As used herein, the terms "target position," "target site," and "target location," refers to a predetermined optimal location for the implant to be placed during the implant procedure, and can be based on the patient's anatomy, condition, diagnosis, prognosis, activity-level, and the like. For example, the target position may be defined by one or more of the following parameters taken in relation to an anatomical landmark: an angle or degree of orientation, and angle or degree of translation, an insertion depth, an insertion angle, degree of contact between two surfaces, and the like. Suitable anatomical landmarks include, for example, specific vertebrae or other recognizable anatomical features. The target position can therefore include a three-dimensional position of the implant relative to patient anatomy (e.g., as defined by boundaries created by patient anatomy), and/or a target orientation of the implant relative to patient anatomy. In some embodiments, the target position may incorporate a desired correction to the patient's native anatomy such that, when the implant is implanted at the target position, it manipulates the patient's anatomy to achieve the desired correction. Without being bound by theory, placing the implant at the target position is expected to optimize the benefit of and/or minimize the side effects of the implant. In particular, the full benefit of the implant may only be realized when the implant is accurately placed at the target position. Various aspects of the implant (e.g., the interbody device and the plate) can have different target positions.

Embodiments of the present disclosure will be described more fully hereinafter with reference to the accompanying drawings in which like numerals represent like elements throughout the several figures, and in which example embodiments are shown.

Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

II. Patient-Specific Vertebral Implants

Figure 1B:
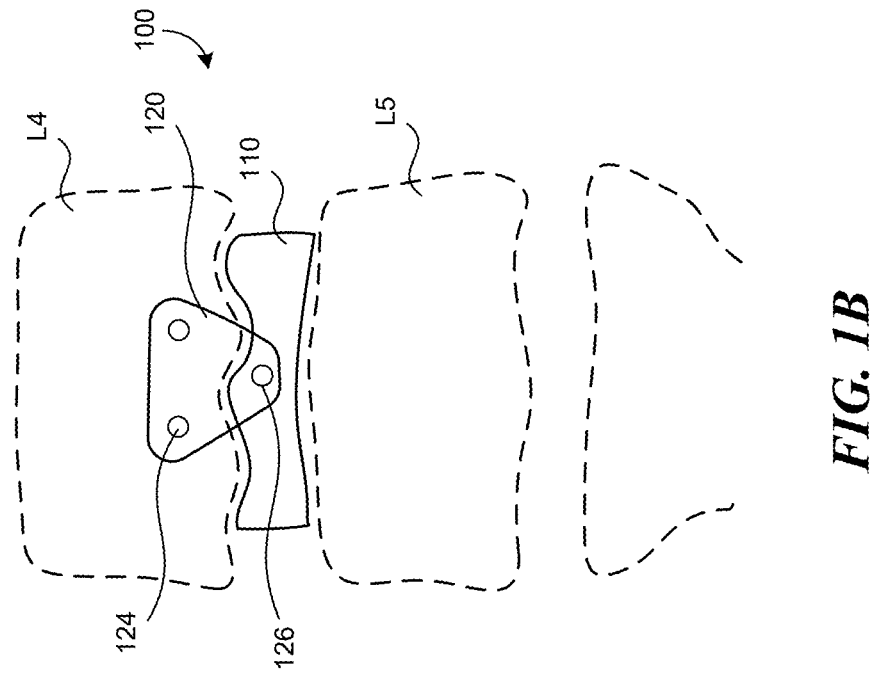
FIG. 1B is a front view of the patient-specific implant of FIG. 1A implanted in the patient's spinal column.
Figure 1A:
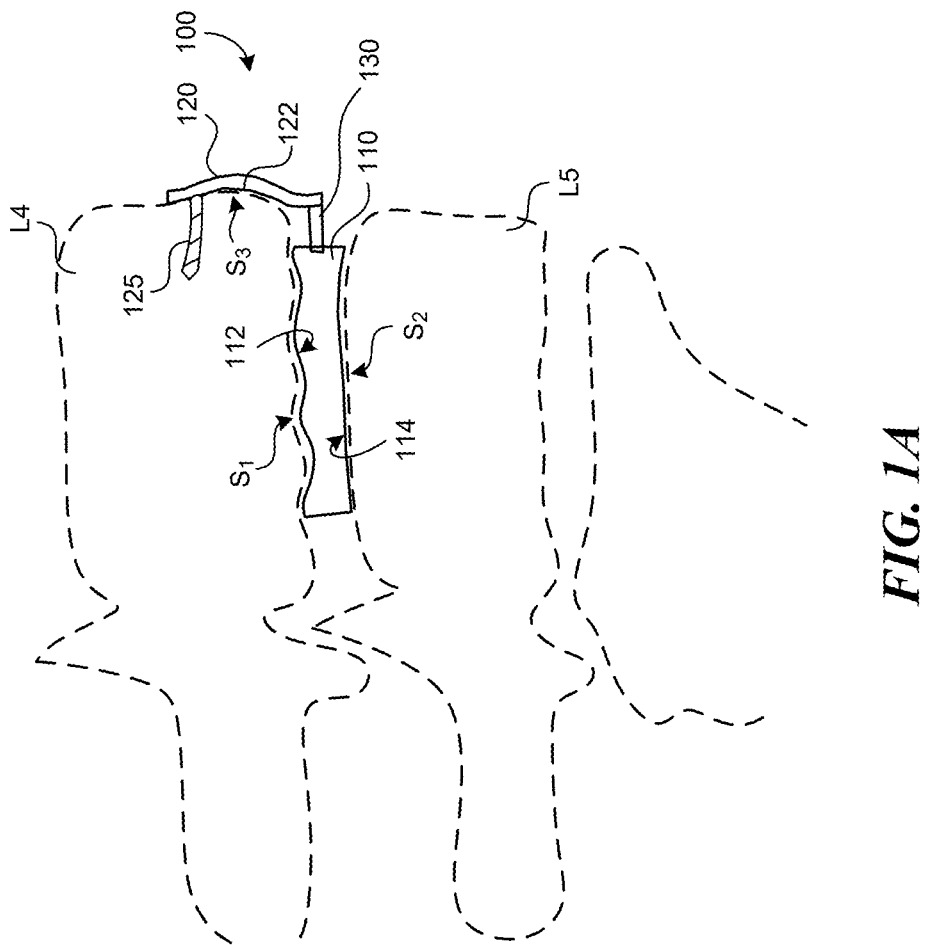
FIG. 1A is a side view of a patient-specific implant implanted in a patient's spinal column and configured in accordance with embodiments of the present technology.

FIGS. 1A and 1B illustrate a patient-specific implant 100 implanted in an intervertebral disc space between L4 and L5 vertebral bodies and configured in accordance with embodiments of the present technology. In particular, FIG. 1A is a side view of the implant 100 implanted between the L4 and L5 vertebral bodies (shown in dashed line), and FIG. 1B is front view of the implant 100 implanted between the L4 and L5 vertebral bodies (shown in dashed line). Referring first to FIG. 1A, the implant 100 includes an interbody element or cage 110, a positioning element or plate 120, and a connection mechanism 130 coupling the cage 110 to the plate 120. The cage 110 is positioned in the disc space between the L4 and L5 vertebral bodies and interfaces with an inferior aspect of the L4 vertebral body and a superior aspect of the L5 vertebral body. The plate 120 is positioned anterior to the vertebral column and contacts an anterior surface of the L4 vertebral body. In other embodiments, the plate 120 can project in an inferior direction and contact an anterior surface of the L5 vertebral body. In some embodiments, and as described with respect to FIGS. 2A and 2B, the plate 120 can project in both an anterior and inferior direction, thus contacting both the L4 and L5 anterior surfaces. In addition to, or in lieu of, having projections extending in an anterior and inferior direction, the plate 220 can include one or more projections that extend laterally and are configured to interface with one or more lateral surfaces of the L4 or L5 vertebral bodies. A fastening element such as a screw 125 can be used to secure the plate 120 to an adjacent anatomical structure, such as the L4 vertebral body, to resist expulsion and/or migration of the cage 110. In some embodiments, and as best shown in FIG. 1B, the plate 120 can include one or more apertures 124 that can receive a portion of the screw 125 for securing the plate 120 to the appropriate vertebral structure.

Returning to FIG. 1A, the cage 110 includes a patient-specific geometry (e.g., size, shape, curvature, contouring, morphology, topography, etc.) designed to mate with the patient's anatomy. As used herein, the term "mate" can refer to the engagement of two surfaces to form a generally gapless interface with reduced and/or minimized empty space therebetween such that at least 80%, 90%, 95%, 97%, 98%, 99%, or 100% of a first surface contacts a second surface in at least some patient orientations (not including any engineered gaps, such as might exist for a chamber included in a central portion of the cage 110). For example, in the illustrated embodiment, a first (e.g., upper) surface 112 of the cage 110 can have a topography designed to mate with a topography of an inferior surface $S_1$ of the L4 vertebral body. When the patient stands and the spine is generally straight, at least 80%, 90%, 95%, 97%, 98%, 99%, or 100% of the surface area of the first surface 112 contacts the inferior surface $S_1$ (e.g., forming a "generally gapless" interface) such that loads are applied generally evenly across the cage 110. In the illustrated embodiment, the inferior surface $S_1$ has a generally "wavy" topography with several recesses and projections. The first surface 112 of the cage 110 therefore has a generally "wavy" topography with several recesses and projections that mate with the generally wavy topography of the inferior surface $S_1$ to form a generally gapless interface therebetween. A second (e.g., lower) surface 114 of the cage 110 can have a topography designed to mate with a topography of a superior surface $S_2$ of the L5 vertebral body. When the patient stands and the spine is generally straight, at least 80%, 90%, 95%, 97%, 98%, 99%, or 100% of the surface area of the second surface 114 can contact the inferior surface $S_2$ (e.g., forming a "generally gapless" interface) such that loads are applied generally evenly across the cage 110. In the illustrated embodiment, the superior surface $S_2$ is generally flat. The second surface 114 of the cage 110 therefore has a generally flat topography to mate with the generally flat topography of the superior surface $S_2$ to form a generally gapless interface therebetween. In the illustrated embodiment, the first surface 112 is shown slightly spaced apart from the inferior surface $S_1$, and the second surface 114 is shown slightly spaced apart from the superior surface $S_2$, to more clearly show the topography of the various surfaces. However, as one skilled in the art will appreciate, the first surface 112 contacts the inferior surface $S_1$ and the second surface 114 contacts the superior surface $S_2$ when the cage 110 is implanted in the patient. In addition to improving the fit of the cage 100, the matching topographies can prevent, inhibit, or limit lateral movement of the cage 110 relative to one or both adjacent vertebrae. For example, the topographies can be designed to keep movement of the cage 110 less than 5%, 2%, or 1% of the maximum length of the inferior surface $S_1$.

The plate 120 also includes a patient-specific geometry (e.g., size, shape, curvature, contouring, morphology, topography, etc.) designed to mate with the patient's anatomy. For example, a contact surface 122 (e.g., a posterior surface) of the plate 120 can have a topography designed to mate with a topography of an anterior surface $S_3$ of the L4 vertebral body. In the illustrated embodiment, the anterior surface $S_3$ is partially curved. The contact surface 122 of the plate 120 is therefore also partially curved to mate with the partially curved topography of the anterior surface $S_3$ to form a generally gapless interface therebetween. In the illustrated embodiment, the contact surface 122 is shown slightly spaced apart from the contact surface $S_3$ to more clearly show the topography of both surfaces. As one skilled in the art will appreciate, the contact surface 122 contacts the anterior surface $S_3$ when the plate 120 is implanted in the patient.

Both the cage 110 and the plate 120 can have a predetermined target position, in which the patient-specific topographies of the cage 110 and the plate 120 mate with their corresponding anatomical structures. For example, the cage 110 is shown in a first target position in which its patient-specific topography aligns with the anatomical structure having the corresponding topography (e.g., the first surface 112 and the second surface 114 align with the inferior surface $S_1$ and the superior surface $S_2$, respectively). In some embodiments, the first target position may be generally centered between the lateral margins of the L4 and L5 vertebral bodies, although other positions are possible. The plate 120 is shown in a second target position in which the patient-specific topography aligns with the anatomical structure having the corresponding topography (e.g., the contact surface 122 aligns with the anterior surface $S_3$). As previously described, placing the cage 110 and the plate 120 at their respective target positions is expected to optimize the benefit of, and/or reduce the side effects associated with, the implant 100. For example, placing the cage 110 in the first target position maximizes the contact between the cage 110 and the L4 and L5 vertebral bodies, which can reduce the risk that the cage is ejected from the disc space between the L4 and L5 vertebral bodies.

The cage 110 can be coupled to the plate 120 via a connection mechanism 130. The connection mechanism 130 can include a rigid or semi rigid interface. For example, and as described in greater detail below with respect to FIGS. 4 and 5, the connection mechanism 130 can include a rigid connection including one or more screws or bolts (e.g., a lag blot, a carriage bolt, a hex bolt, a machine screw, a wood screw, etc.), a rigid metal arm, etc. Semi-rigid connections can include a semi-rigid metal arm (e.g., a slotted arm, a flexible arm, etc.), arm with cut-out or bend points, etc. In some embodiments, the connection mechanism 130 can be a key and slot mechanism, a magnet, a rivet, a tether, or other suitable fastening element(s). In some embodiment, and as best shown in FIG. 1B, the plate 120 can include an aperture 126 or other feature to facilitate connection of the plate 120 to the cage 110. As described in greater detail below with respect to FIG. 6, the cage 110 and the plate 120 are coupled via the connection mechanism 130 before being delivered to the intervertebral disc space. In other embodiments, and as described in greater detail below with respect to FIG. 7, the cage 110 and the plate 120 can be delivered to the intervertebral disc space in an uncoupled state, and the connection mechanism 130 can be used to mechanically couple the cage 110 and the plate 120 once both are implanted.

The spatial relationship (e.g., a one-dimensional relationship, a two-dimensional relationship, or the three-dimension relationship) of the cage 110 relative to the plate 120 therefore depends at least in part on the connection mechanism 130. As will be described in greater detail below, the desired spatial relationship between the cage 110 and the plate 120 following implantation depends on the relative location of the first target position and the second target position. The connection mechanism 130 can be therefore be designed to connect the cage 110 to the plate 120 to form the specific dimensional spatial relationship that simultaneously permits the cage 110 to occupy the first target position and the plate 120 to occupy the second target position. For example, the connection mechanism 130 can be in the form of a flexible tether that maintains a one-dimensional spatial relationship (e.g., a maximum distance from the cage to the plate 120). By way of another example, the connection mechanism 130 can be a semi-rigid arm capable of flexing in the inferior and superior direction to allow a desired level of flexion of the spine. The semi-rigid arm can maintain a two-dimensional relationship between the cage 110 and plate 120 to limit or prevent lateral movement of the cage 110.

Figures 2A, 2B:
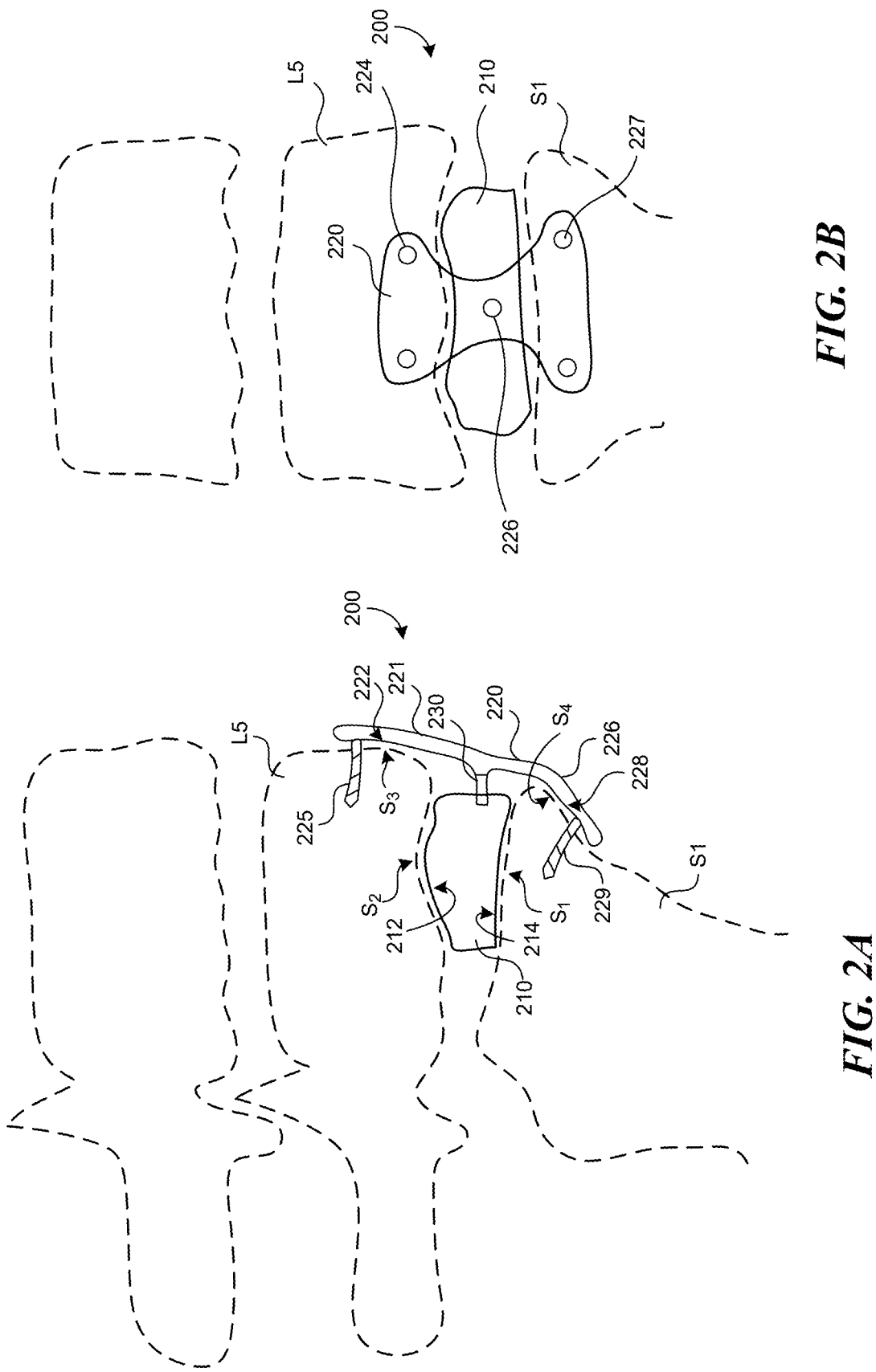
FIG. 2A is a side view of another patient-specific implant implanted in a patient's spinal column and configured in accordance with embodiments of the present technology.
FIG. 2B is a front view of the patient-specific implant of FIG. 2A implanted in the patient's spinal column.

FIGS. 2A and 2B illustrate another patient-specific implant 200 implanted in an intervertebral disc space between L5 and $S_1$ vertebral bodies and configured in accordance with embodiments of the present technology. In particular, FIG. 2A is a cross-sectional side view of the implant 200 implanted between the L5 and $S_1$ vertebral bodies (shown in dashed line), and FIG. 2B is front view of the implant 200 implanted between the L5 and $S_1$ vertebral bodies (shown in dashed line). The implant 200 can include certain features generally similar to the implant 100 described above with respect to FIGS. 1A and 1B. For example, referring first to FIG. 2A, the implant 200 includes a patient-specific interbody element or cage 210, a patient-specific positioning element or plate 220, and a connection mechanism 230 coupling the cage 210 to the plate 220. The cage 210 is positioned in the disc space between L5 and $S_1$ and is configured to interface with an inferior aspect of the L5 vertebral body and a superior aspect of the $S_1$ vertebral body. The plate 220 is positioned anterior to the vertebral column.

The cage 210 can be generally similar to the cage 110 described in detail with respect to FIGS. 1A and 1B. For example, a first (e.g., upper) surface 212 of the cage 210 can have a topography designed to mate with a topography of an inferior surface $S_2$ of the L5 vertebral body, and a second (e.g., lower) surface 214 can have a topography designed to mate with a topography of a superior surface $S_1$ of the $S_1$ vertebral body (the geometry of the cage 210 is shown as different than the geometry of the cage 110 in FIG. 1 to demonstrate inter-patient anatomical variability, which further illustrates the need for the patient-specific implants described herein).

Unlike the plate 120 shown in FIGS. 1A and 1B, the plate 220 projects in both a superior and inferior direction, and therefore contacts both an anterior surface of the L5 vertebral body and an anterior surface of the $S_1$ vertebral body. In particular, the plate 220 includes a first (e.g., superior) projection or wing 221 and a second (e.g., inferior) projection or wing 226. The first projection 221 includes a first contact surface 222 that is configured to interface with an anterior surface $S_3$ of the L5 vertebral body. As described in detail with respect to FIG. 1A, the first contact surface 222 can have a patient-specific geometry (e.g., size, shape, curvature, contouring, morphology, topography, etc.) designed to mate with the anterior surface $S_3$. The first projection 221 can also include one or more apertures 224 (FIG. 2B) for receiving one or more fastening elements or screws 225 (FIG. 2A) for securing the plate 220 to the L5 vertebral body to resist expulsion and/or migration of the cage 210. The second projection 226 includes a second contact surface 228 configured to interface with an anterior surface $S_4$ of the $S_1$ vertebral body. The second contact surface 228 can also have a patient-specific geometry designed to mate with the anterior surface $S_4$. Notably, because the second projection 226 is configured to mate with a different surface than the first projection 221, the second projection 226 may have a different geometry than the first projection 221. The second projection 226 can also include one or more apertures 227 (FIG. 2B) for receiving one or more fastening elements or screws 229 (FIG. 2A) for securing the plate 220 to the $S_1$ vertebral body to resist expulsion and/or migration of the cage 210. In some embodiments, incorporating multiple wings/projections into the plate 220 can provide fixation between adjacent vertebral bodies to reduce post-operative motion between the vertebral bodies, as well as increasing the stability provided by the plate 220 to reduce migration and/or expulsion of the cage 210.

In addition to, or in lieu of, having projections extending in an anterior and inferior direction, the plate 220 can include one or more projections that extend laterally and are configured to interface with one or more lateral surfaces of the L5 or $S_1$ vertebral bodies. In such embodiments, the lateral projections can have a patient-specific geometry that is configured to mate with a lateral surface of the L5 and/or $S_1$ vertebral bodies. The lateral projections can also be used to secure the plate 220 to the vertebral bodies.

Figure 3B:
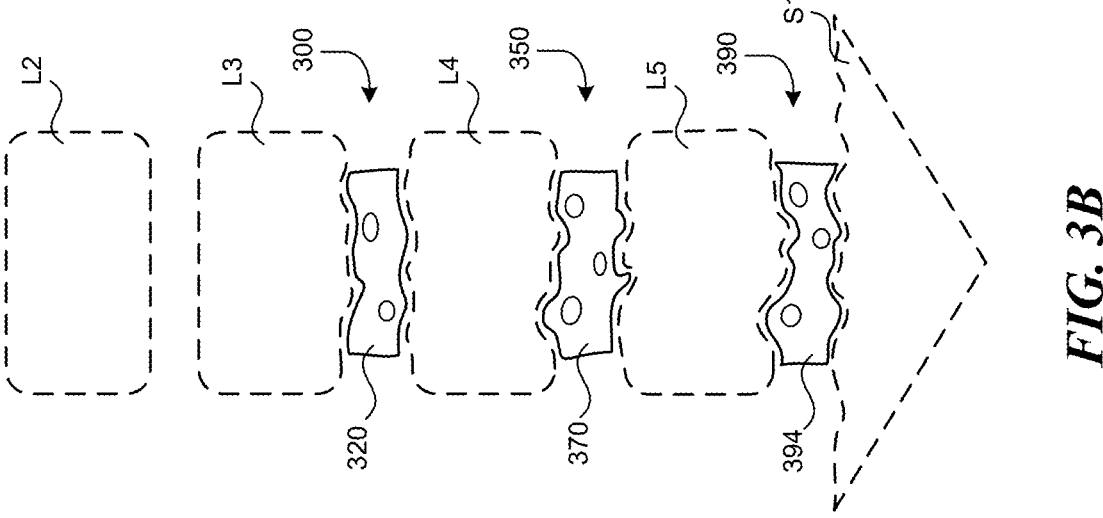
FIG. 3B is a front view of the plurality of patient-specific implants of FIG. 3A implanted in the patient's spinal column.
Figure 3A:
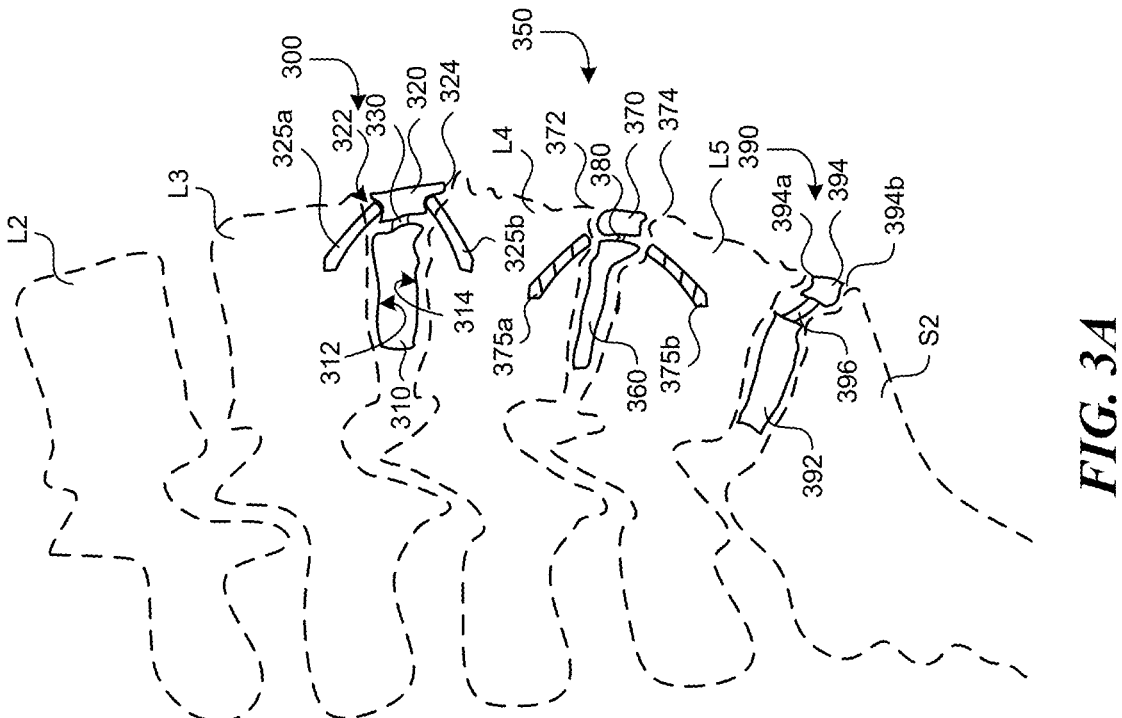
FIG. 3A is a side view of a plurality of patient-specific implants implanted in a patient's spinal column and configured in accordance with embodiments of the present technology.

FIGS. 3A and 3B illustrate additional patient-specific implants implanted in an intervertebral disc space bodies and configured in accordance with embodiments of the present technology. More specifically, FIGS. 3A and 3B illustrate three patient-specific implants: implant 300 implanted between the L3 and L4 vertebral bodies (shown in dashed line), implant 350 positioned between the L4 and L5 vertebral bodies (shown in dashed line), and implant 390, positioned between the L5 and $S_1$ vertebral bodies (shown in dashed line). Although the implants 300, 350, and 390 are shown as implanted in the same spine, one skilled in the art will appreciate that implants 300, 350, and 390 can be used alone and/or in combination with other implants beyond those shown.

The implants 300, 350, and 390 can include certain features generally similar to the implants 100, 200 previously described. For example, the implant 300 can include an interbody element or cage 310, a positioning element or plate 320, and a connection mechanism 330 coupling the cage 310 to the plate 320. The cage 310 of the implant 300 is positioned at a first target position in the disc space between the L3 and L4 vertebral bodies and is configured to interface with an inferior aspect of the L3 vertebral body and a superior aspect of the L4 vertebral body. As described previously with respect to the implants 100, 200, the cage 310 can include a patient-specific geometry (e.g., size, shape, curvature, contouring, morphology, topography, etc.) designed to mate with the corresponding patient anatomy at the first target position. For example, an upper surface 312 of the cage 310 can be designed with a geometry/topography that mates with an inferior surface of the L3 vertebral body, and a lower surface 314 of the cage 310 can be designed with a geometry/topography that mates with a superior surface of the L4 vertebra body. In the illustrated embodiment, the upper surface 312 is shown slightly spaced apart from the inferior surface of the L3 vertebral body, and the lower surface 314 is shown slightly spaced apart from the superior surface of the L4 vertebral body, to more clearly show the topography of the various surfaces. However, as one skilled in the art will appreciate, the upper surface 312 contacts the inferior surface of the L3 vertebral body and the lower surface 314 contacts the superior surface of the L4 vertebral body when the cage 110 is implanted in the patient.

The plate 320 can also have a patient-specific geometry configured to mate with the corresponding patient anatomy at a second target position. However, unlike the plates 120, 220 described with respect to FIGS. 1A-2B, the plate 320 is configured to reside substantially within the disc space between the L3 and L4 vertebral bodies. For example, in some embodiments the plate 320 does not extend beyond the anterior and/or lateral margins of the L3 and/or L4 vertebral bodies. The plate 320 therefore has an upper (e.g., superior) surface 322 having a geometry/topography designed to mate with an inferior surface of the L3 vertebral body and/or an anterior or lateral margin of the L3 vertebral body. The plate 320 has a lower (e.g. inferior) surface 324 having a geometry/topography designed to mate with a superior surface of the L4 vertebral body and/or an anterior or lateral margin of the L4 vertebral body. The plate 320 can be secured in position using a first fastening element or screw 325a projecting from the upper surface 322 and a second fastening element or screw 325b projecting from the lower surface 324, thereby resisting expulsion and/or migration of the cage 310. In some embodiments, the features 325a, 325b are arms or anchors that can be driven into the vertebral bodies. One expected advantage of designing the plate 320 to be positioned substantially within the disc space is reducing the overall profile of the implant 300, which may aid in delivery of the implant 300 and/or in the long-term efficacy of the implant 300.

The implants 350 and 390 can be generally similar to the implant 300. For example, the implant 350 can include an interbody element or cage 360, a positioning element or plate 370, and a connection mechanism 380 coupling the cage 360 to the plate 370. The cage 360, the plate 370, and/or the connection mechanism 380 can have patient-specific features (e.g., geometry, topography, etc.), such as any of the patient-specific features previously described herein.

The implant 390 can also be generally similar to the implant 300 and the implant 350. For example, the implant 390 can include an interbody element or cage 392, a positioning element or plate 394, and a connection mechanism 396. The cage 392, the plate 394, and/or the connection mechanism 396 can have patient-specific features (e.g., geometry, topography, etc.), such as any of the patient-specific features previously described herein. Relative to the implants 300, 350, the implant 390 does not include additional fastening elements or screws. Rather, the implant 390 is secured in position solely based on its frictional interface with the adjacent vertebrae. For example, an upper surface 394a of the plate 394 can have a geometry/topography designed to mate with an inferior surface of the L5 vertebral body and/or an anterior or lateral margin of the L5 vertebral body, and a lower surface 394b of the plate 394 can have a geometry/topography designed to mate with a superior surface of the $S_1$ vertebral body and/or an anterior or lateral margin of the $S_1$ vertebral body.

Although the implants in FIGS. 1A-3B are shown as implanted between specific vertebral bodies (e.g., the implant 100 is shown as implanted between the L4 and L5 vertebral bodies), one skilled in the art will appreciate that the implants described herein can be designed to be implanted between other vertebral bodies, including those in the cervical, thoracic, and lumbar regions. Moreover, although the implants shown in FIGS. 1A-3B include a "cage" and a "plate", the present technology is not limited to such embodiments. Rather, the present technology can include other types of interbody devices and orthopedic implants. Additionally, because the implants described herein are designed to match individual patient anatomy, the size, shape, and geometry of the implants will vary according to individual patient anatomy. The present technology is thus not limited to any particular implant design or configuration, and can therefore include other implants beyond those expressly illustrated or described herein.

FIG. 4 illustrates a patient-specific implant 400 configured in accordance with embodiments of the present technology. The implant 400 can be generally similar to any of the patient-specific implants previously described. For example, the implant 400 can include an interbody element or cage 410, a positioning element or plate 420, and a connection mechanism 430 configured to couple the cage 410 to the plate 420. The cage 410, the plate 420, and/or the connection mechanism 430 can have patient-specific features (e.g., geometry, topography, etc.), such as any of the patient-specific features previously described herein. The plate 420 can have one or more apertures 424 that extend between a first (e.g., outer) surface 423 and a second (e.g., inner) surface 422. Once the implant 400 is implanted in a patient, one or more screws (not shown) can be inserted through the apertures 424 and secured to an anatomical structure (e.g., screwed into one or more vertebral bodies).

As illustrated, certain aspects of the connection mechanism 430 can be integral with the plate 420. For example, the plate 420 can be connected to or include an integral projection 432 (e.g., arm, extension, lever, etc.) that extends transversely from the plate 420. The projection 432 can have a hollow interior defining a lumen or other opening 434 that is aligned with an aperture 426 extending through the plate 420. As described below, a screw or other fastening element (e.g., a lag blot, a carriage bolt, a hex bolt, a machine screw, a wood screw, etc.) can be inserted into the lumen 434 via the aperture 426. A distal end portion of the projection 432 can fit within a corresponding recess or receiving feature 416 in the cage 410. The recess 416 may have a receiver 417, which in some embodiments defines a threaded female connector for receiving a corresponding threaded male connector. The receiver 417 aligns with the lumen 434 when the projection 432 is advanced into the recess 416. The screw or other fastening element can be inserted through the aperture 426 of the plate 420, advanced through the lumen 434 of the projection 432, and secured (e.g., threadably secured) to the receiver 417, thereby securing the plate 420 to the cage 410.

Additionally or alternatively, the connection mechanism 430 can couple the plate 420 to the cage 410 using other suitable mechanisms. For example, in some embodiments the receiver 417 may comprise one or more magnets that adhere to the distal end portion of the projection 432 when it is inserted into the recess 416 to magnetically couple the plate 420 to the cage 410. As another example, the connection mechanism 430 can utilize a key and slot mechanism, in which the projection includes one or more features configured to releasably engage one or more features in the recess 416 to releasably couple the plate 420 to the cage 410. In yet other embodiments, the plate 420 can be coupled to the cage 410 using a rivet, a tether, or another suitable connection mechanism.

In some embodiments, the connection mechanism 430 can form a rigid (e.g., inelastic) interface between the plate 420 and the cage 410 that minimizes and/or reduces strain in response to external stresses. For example, the connection mechanism 430 may be rigid so as to retain a predetermined three-dimensional orientation between the cage 410 and the plate 420 even if one or both of the cage 410 or the plate 420 is subjected to mechanical stress. In embodiments in which the connection mechanism 430 is rigid, the connection mechanism 430 may include one or more metal screws or bolts extending substantially the entire length of the projection 432.

In some embodiments, the connection mechanism 430 can form a semi-rigid interface between the plate 420 and the cage 410 to minimize strain in response to external stresses while permitting some degree of relative motion between the plate 420 and the cage 410 to account for changes in patient anatomy during patient motion. For example, in some embodiments the connection mechanism 430 may permit motion of up to 5 degrees, 10 degrees, 15 degrees, etc. in at least one plane of motion. In embodiments in which the connection mechanism 430 is semi-rigid, one or more aspects of the connection mechanism 430 (e.g., the projection 432) can be composed of an at least partially elastic or flexible material (e.g., nitinol, silicone, rubber, etc.) and/or include one or more motion segments or joints.

Regardless of its composition, the connection mechanism 430 provides a specific (e.g., patient-specific) three-dimensional spatial relationship/orientation between the plate 420 and the cage 410 when the plate 420 is coupled to the cage 410 via the connection mechanism 430. Accordingly, the projection 432, the recess 416, and other associated features can be specifically designed such that, when the plate 420 is secured to the cage 410, the plate 420 and the cage 410 assume a predetermined orientation and position relative to each other. In particular, because the cage 410 is designed to be implanted at a first target position and the plate 420 is designed to be implanted at a second target position, coupling the plate 420 to the cage 410 causes the plate 420 and the cage 410 to assume an orientation that enables the cage 410 to be in the first target position and simultaneously allows the plate 420 to be in the first target position. As a result, and as described in more detail later, coupling the plate 420 to the cage 410 when the plate 420 is at the second target position forces the plate 420 and the cage 410 into the predetermined orientation, which can direct the cage 410 to occupy the first target position.

FIG. 5 illustrates a patient-specific implant 500 configured in accordance with embodiments of the present technology. The implant 500 can be generally similar to any of the patient-specific implants previously described. For example, the implant 500 can include an interbody element or cage 510, a positioning element or plate 520, and a connection mechanism 530 configured to couple the cage 510 to the plate 520. The cage 510, the plate 520, and/or the connection mechanism 530 can have patient-specific features (e.g., geometry, topography, etc.), such as any of the patient-specific features previously described herein. The plate 520 can have one or more apertures 524 that extend between a first (e.g., outer) surface 523 and a second (e.g., inner) surface 522. Once the implant 500 is implanted in a patient, one or more screws can be inserted through the apertures 524 and secured to an anatomical structure (e.g., screwed into one or more vertebral bodies).

As with the connection mechanism 430 of the implant 400, certain aspects of the connection mechanism 430 can be integral with the plate 420. For example, the plate 520 can be connected to or include an integrated projection 532 (e.g., arm, extension, lever, etc.) that extends transversely from the plate 520. The projection 532 can have a hollow interior defining a lumen or other opening 534 that is aligned with an aperture 526 in the plate 520. Unlike the connection mechanism 430 of the implant 400, the cage 510 does not include a recess for slidable receiving a distal end portion of the projection 532. Rather, the cage 510 includes a threaded receiver 517 defining a threaded female connector for receiving a corresponding threaded male connector. The threaded receiver 517 extends inwardly from an outer surface of the cage 510 (as opposed to extending inwardly from a recess, such as the recess 416 shown in FIG. 4). Once the projection 532 is generally aligned with the threaded receiver 517, a screw or other fastening element (not shown) can be inserted through the aperture 526 of the plate 520, advanced through the lumen 534 of the projection 532, and threadably secured to the threaded receiver 517 to secure the plate 520 to the cage 510.

In some embodiments, the connection mechanism 530 can form a rigid (e.g., inelastic) and/or semi-rigid connection interface between the plate 520 and the cage 510 that minimizes and/or reduces strain in response to external stresses. For example, the connection mechanism 530 may retain a predetermined three-dimensional orientation between the cage 510 and the plate 520 even if one or both of the cage 510 or the plate 520 is subjected to mechanical stress.

Similar to the connection mechanism 430, the connection mechanism 530 provides a specific (e.g., patient-specific) three-dimensional spatial relationship/orientation between the plate 520 and the cage 510. Accordingly, the projection 532, the threaded receiver 517, and other associated features can be designed with an orientation such that, when the plate 520 is secured to the cage 510, the plate 520 and the cage 510 assume a predetermined orientation and position relative to each other. In particular, because the cage 510 is designed to be implanted at a first target position and the plate 520 is designed to be implanted at a second target position, coupling the plate 520 to the cage 510 causes the plate 520 and the cage 510 to assume an orientation that enables the cage 510 to be in the first target position and simultaneously allows the plate 520 to be in the first target position. As a result, and as described in more detail below, coupling the plate 520 to the cage 510 when the plate 520 is at the second target position forces the plate 520 and the cage 510 into the predetermined orientation, which can direct the cage 510 to occupy the first target position.

III. Methods for Implanting Patient-Specific Vertebral Implants

The present technology also provides methods for implanting patient-specific vertebral devices to a target region at or proximate a patient's spine. FIG. 6 is a flowchart of a method 600 for implanting a patient-specific vertebral implant having a cage and a plate in a coupled state to a target region at or proximate a patient's spine. The method 600 can include, in step 602, providing a patient-specific implant having a cage and a plate. The cage is generally designed with patient-specific features (e.g., geometry, topography, etc.) configured to mate with a first identified anatomical structure at a first target position. The first target position is generally in the disc space between adjacent vertebral bodies, and the first identified anatomical structural is generally an inferior surface of a superior vertebral body and/or a superior surface of an inferior vertebral body. The plate is also generally designed with patient-specific features (e.g., geometry, topography, etc.) configured to mate with a second identified anatomical structure at a second target position. The second target position is generally adjacent an anterior surface of the vertebral column, a lateral surface of the vertebral column, and/or at an anterior margin of the disc space between adjacent vertebral bodies. Accordingly, the second identified anatomical structure is generally an anterior or lateral surface of a vertebral body, and/or an inferior surface of a superior vertebral body and/or a superior surface of an inferior vertebral body.

The method 600 can continue in step 604 by coupling the plate to the cage, such as via any of the connection mechanisms described herein. Step 604 is performed before the implant is implanted into the patient, and can be performed by a surgeon, a surgical robotic platform, and/or a surgeon assisted by a surgical robotic platform. In some embodiments, for example, the plate and cage are manufactured as separate components and are coupled together in the operating room as part of the pre-operative procedure. In other embodiments, the plate and the cage can be manufactured in a coupled state (e.g., the plate and the cage can be a unitary or integral component). In such embodiments, the step 604 can be omitted, and the method 600 can proceed from step 602 directly to step 606. Regardless, once coupled, the cage and plate can assume a predetermined three-dimensional orientation that enables the cage to occupy a first target position and the plate to simultaneously occupy a second target position.

The method 600 continues in step 606 by delivering (e.g., implanting) the implant to the target region at or proximate the patient's spine. With the implant at or adjacent the target region, the method 600 continues in step 608 by positioning the plate at the second target position. This can be done by a surgeon, a surgical robotic platform, and/or a surgeon assisted by a surgical robotic platform. In some embodiments, a surgeon performing or otherwise assisting with the surgery can directly visualize the second target position, enabling the surgeon to accurately position the plate at the second target position. In some embodiments, because the plate has a patient-specific topography/geometry configured to mate with the second anatomical structure at the second target position, the surgeon will be able to tell when the plate is at the second target position based on the physical interaction between the plate and the second anatomical structure (e.g., the plate "fits" with the second anatomical structure when placed at the second target position). In some embodiments, the plate can be secured at the second target position by inserting a screw or other fastening element through one or more apertures in the plate and into the second identified anatomical structure.

Because the plate is coupled to the cage in a predetermined three-dimensional orientation, positioning the plate at the second target position directs the cage to occupy the first target position. Accordingly, positioning the plate at the second target position also positions (e.g., automatically positions) the cage at the first target position. Without being bound by theory, placing the cage and plate at their respective target positions is expected to optimize the benefit of and/or minimize the side effects of the implant. In particular, the full benefit of the implant may only be realized when the implant is accurately placed at the target position. The method 600 can optionally continue in step 610 by confirming that the cage is in the first target position. The position of the cage can be confirmed using one or more conventional imaging technologies known in the art (e.g., X-Ray, MRI, CT-scan, etc.).

FIG. 7 is a flowchart of a method 700 for implanting a patient-specific vertebral implant having a plate and a cage in an uncoupled state to a target region at or proximate a patient's spine. The method 700 can include, in step 702, providing a patient-specific implant having a cage and a plate. The cage is generally designed with patient-specific features (e.g., geometry, topography, etc.) configured to mate with a first identified anatomical structure at a first target position. The first target position is generally in the disc space between adjacent vertebral bodies, and the first identified anatomical structural is generally an inferior surface of a superior vertebral body and/or a superior surface of an inferior vertebral body. The plate is also generally designed with patient-specific features (e.g., geometry, topography, etc.) configured to mate with a second identified anatomical structure at a second target position. The second target position is generally adjacent an anterior surface of the vertebral column, a lateral surface of the vertebral column, and/or at an anterior margin of the disc space between adjacent vertebral bodies. Accordingly, the second identified anatomical structure is generally an anterior or lateral surface of a vertebral body, and/or an inferior surface of a superior vertebral body and/or a superior surface of an inferior vertebral body.

The method 700 can continue in step 704 by delivering (e.g., implanting) the cage to a location proximate the first target position, and in step 706 by delivering (e.g., implanting) the plate to a location proximate the second target position. Steps 704 and 706 can be performed by a surgeon, a surgical robotic platform, and/or a surgeon assisted by a surgical robotic platform. However, unlike described above with respect to method 600, the cage and the plate are not coupled together before delivering the cage to the target position in the method 700. Without being bound by theory, delivering the cage and the plate in an uncoupled state is expected to increase the maneuverability of these components and/or reduce the size of the surgical corridor needed to deliver these components to the spinal cord region.

The method 700 can continue in step 708 by positioning the plate at the second target position. This can also be performed by a surgeon, a surgical robotic platform, and/or a surgeon assisted by a surgical robotic platform. In some embodiments, a surgeon performing or otherwise assisting with the surgery can directly visualize the second target position, enabling the surgeon to accurately position the plate at the second target position. In some embodiments, because the plate has a patient-specific topography/geometry configured to mate with the second anatomical structure at the second target position, the surgeon will be able to tell when the plate is at the second target position based on the physical interaction between the plate and the second anatomical structure (e.g., the plate "fits" with the second anatomical structure when placed at the second target position). In some embodiments, the plate can be secured at the second target position by inserting a screw or other fastening element through one or more apertures in the plate and into the second identified anatomical structure.

Once the plate is in the second target position, the method 700 continues in step 710 by coupling (e.g., mechanically coupling) the plate to the cage. The plate can be coupled to the cage using any of the connection mechanisms previously described herein. Because the plate and cage assume a predetermined three-dimensional orientation when coupled, coupling the plate to the cage when the plate is positioned at the second target position directs the cage to occupy the first target position. Accordingly, coupling the plate to the cage positions (e.g., automatically positions) the cage at the first target position. In some embodiments, the steps 708 and 710 can be reversed such that the plate is coupled to the cage before positioning the plate at the second target position. In such embodiments, once the cage and plate are coupled, positioning the plate at the second target position directs the cage to occupy the first target position. As previously described, positioning the cage and plate at their respective target positions is expected to optimize the benefit of and/or minimize the side effects of the implant. In particular, the full benefit of the implant may only be realized when the implant is accurately placed at the target position. The method 700 can optionally continue in step 712 by confirming that the cage is in the first target position. The position of the cage can be confirmed using one or more conventional imaging technologies known in the art (e.g., X-Ray, MRI, CT-scan, etc.).

As one skilled in the art will appreciate from the foregoing description, the present technology utilizes the patient-specific nature of the implant components (e.g., the plate and the cage) to make it easier to position the cage at the first target position. For example, because the cage and the plate are coupled together in a predetermined three-dimensional orientation, positioning the plate at the second target position directs the cage toward and/or to the first target position. Thus, positioning the plate at the second target position also positions the cage at the first target position. Without being bound by theory, it is generally easier for a surgeon to position the plate at the second target position than it is to position the cage at the first target position. For example, plates are typically positioned along an anterior surface of the vertebral column and/or at an anterior margin of the disc space that is generally visible to the surgeon, whereas cages are typically positioned at a location in the disc space out of view of the surgeon. Therefore, by mechanically coupling the plate and cage in a predetermined three-dimensional orientation, the surgeon can simply position the plate at the easier-to-visualize second target position, simplifying the implant procedure. The patient-specific nature of the implants provides additional benefits, such as improved fit, improved outcomes, and/or reduced side effects, as previously described.

IV. Systems and Methods for Designing, Manufacturing, and Implanting Patient-Specific Implants The present technology also provides system and methods for designing and manufacturing patient-specific implants, such as any of the patient-specific vertebral implants described herein. FIG. 8 is a network connection diagram illustrating a computing system 800 for providing patient-specific medical care and configured in accordance with select embodiments of the present technology. The system 800 is configured to design a patient-specific implant and/or generate a patient-specific surgical plan for a patient. For example, the system 800 can generate an implant and/or generate a surgical plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof. The surgical plan can include surgical information, surgical plans (e.g., surgical implant procedure, target implant location and/or orientation, etc.), technology recommendations (e.g., device and/or instrument recommendations), and/or medical device designs. For example, the surgical plan can include at least one treatment procedure (e.g., a surgical procedure or intervention) and/or at least one medical device (e.g., an implanted medical device (also referred to herein as an "implant" or "implanted device") or implant delivery instrument).

The system 800 includes a computing device 802, which can be a user device, such as a smart phone, mobile device, laptop, desktop, personal computer, tablet, phablet, or other such devices known in the art. As discussed in greater detail with reference to FIG. 9, the computing device 802 can include one or more processors, and memory storing instructions executable by the one or more processors to perform select methods described herein. The computing device 802 can be associated with a healthcare provider that is treating the patient. Although FIG. 8 illustrates a single computing device 802, in alternative embodiments, the computing device 802 can instead be implemented as a computing system encompassing a plurality of computing devices, such that the operations described herein with respect to the computing device 802 can instead be performed by the computing system and/or the plurality of computing devices.

The computing device 802 is configured to receive a patient data set 808 associated with a patient to be treated. The patient data set 808 can include data representative of the patient's condition, anatomy, pathology, symptoms, medical history, preferences, and/or any other information or parameters relevant to the patient. For example, the patient data set 808 can include surgical intervention data, treatment outcome data, progress data (e.g., physician notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 808 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

In some embodiments, the computing device 802 can also be configured to receive a surgical team data set 810. The surgical team data set 810 can include data representative of the surgical team that will perform the surgery on the patient. For example, the surgical team data set 810 can include preferences of the surgical team (e.g., preferred implant techniques, preferred implant instruments/tools, etc.), experience of the surgical team (e.g., past procedures performed by the surgical team), scored outcomes of past procedures performed by the surgical team, or the like. As used herein, the term "surgical team" can refer to a group of healthcare practitioners that work together in an operating room during an implant procedure, or to one or more individual surgeons.

In some embodiments, the computing device 802 can also be configured to receive a facility or provider data set 812. The facility data set 812 can include data representative of the facility at which the patient's surgery will occur. For example, the facility data set 812 can include preferences of the facility (e.g., preferred implant techniques, preferred implant instruments/tools, etc.), experience of the facility (e.g., past procedures performed at the facility), scored outcomes of past procedures performed at the facility, infrastructure available to assist/perform the surgery (e.g., availability of robotic surgical platforms, as well as the type of "input" required to control the "output" of the robotic surgical platforms), or the like. As used herein, the term "facility" can refer to a single operating room facility, a hospital having multiple operating rooms, and/or a network of hospitals.

The computing device 802 is operably connected via a communication network 804 to a server 806, thus allowing for data transfer between the computing device 802 and the server 806. The communication network 804 may be a wired and/or a wireless network. The communication network 804, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 806, which may also be referred to as a "treatment assistance network" or "prescriptive analytics network," can include one or more computing devices and/or systems. As discussed further herein, the server 806 can include one or more processors, and memory storing instructions executable by the one or more processors to perform the methods described herein. In some embodiments, the server 806 is implemented as a distributed "cloud" computing system or facility across any suitable combination of hardware and/or virtual computing resources.

The computing device 802 and/or the server 806 can design a patient-specific implant ("implant") based at least in part on the patient data set 808, the surgical team data set 810, and/or the facility data set 812. For example, the server 806 may include a treatment planning module 818 that can design, based off on any of the foregoing data inputs, the implant. In some embodiments, the implant includes a design for a vertebral implant including a cage and a plate, such as any of the vertebral implants described with respect to FIGS. 1A-5, that are specifically designed to mate with corresponding target anatomical structures. The computing device 802 and/or the server 806 can design an interbody device (e.g., a cage), a positioning feature (e.g., a plate), a connection mechanism, and/or one or more fastening elements (e.g., a screw). For example, to design the connection mechanism, the target position of the cage can be determined by analyzing images of the patient. The patient spine can be analyzed to identify a suitable target site for the positioning feature. For example, the vertebral bodies can be analyzed to identify regions with suitable geometry and mechanical properties to interface with a locking plate. The computing device 802 and/or the server 806 can design the connection mechanism based on a level of movement (e.g., a maximum level of relative movement) between the cage and the locking plate. In spinal fusion procedures, the connection mechanism can be a rigid arm that substantially prevents relative movement between the cage and the plate. In articulating disc procedures, the implant can include an articulating disk, a plate, and one or more flexible or semi rigid connection mechanisms coupling the disk and plate together. The target spatial relationship between the components of the implant can be determined based on the patient data and targeted outcome.

Additional implants include, but are not limited to, screws (e.g., bone screws, spinal screws, pedicle screws, facet screws), other interbody implant devices, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.).

The implant can be designed to match the patient's existing anatomy. For example, the implant can be designed such that various surfaces of the implant mate with corresponding surfaces of patient anatomy, as previously described. In some embodiments, the implant can be designed to provide a correction to the patient's existing anatomy in addition to mating with one or more surfaces of the patient anatomy. For example, the treatment planning module 818 may analyze image data of the patient's native anatomy to determine whether an anatomical correction is needed. The image data may show the patient's native anatomical configuration (e.g., pre-operative anatomy), such as the geometry, orientation, and topography of various anatomical features. In some embodiments, for example, the image data may show (and/or be used to determine) various anatomical characteristics, including, but not limited to, vertebral spacing, vertebral orientation, vertebral translation, abnormal bony growth, abnormal joint growth, joint inflammation, joint degeneration, tissue degeneration, stenosis, scar tissue, lumbar lordosis, Cobb angle(s), pelvic incidence, disc height, segment flexibility, rotational displacement, and other spinal tissue characteristics. If an anatomical correction is not required, the treatment planning module 818 can design the implant to fit the patient's native anatomy. If an anatomical correction is required, the treatment planning module 818 can design the implant such that, when the implant is implanted in the patient, it provides the anatomical correction. Additional details for designing patient-specific implants to provide one or more desired anatomical corrections can be found in U.S. application Ser. No. 16/987,113, filed Aug. 6, 2020, the disclosure of which is incorporated by reference herein in its entirety.

In some embodiments, the generated implant design is a design for an entire device. Alternatively, the generated design can be for one or more components of a device (e.g., a plate or a cage), rather than the entire device. In some embodiments, the implant design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The implants described herein are expected to improve delivery into the patient's body, placement at the treatment site, and/or interaction with the patient's anatomy.

The computing system 802 and/or the server 806 can also design a patient-specific surgical plan ("surgical plan") based on the patient data set 808, the surgical team data set 810, and/or the facility data set 812. The surgical plan can include a detailed procedure for implanting the implant to a specific target position within the patient. For example, the surgical plan can include aspects of a pre-operative plan (e.g., detection and measurement of patient's anatomy, preparation of patient for a surgical procedure, etc.), a surgical procedure, a surgical approach (e.g., implant technique), one or more surgical steps (preparing tissue for an incision, making an incision, making a resection, removing tissue, manipulating tissue, performing a corrective maneuver, delivering the implant to a target site, deploying the implant at the target site, adjusting the implant at the target site, manipulating the implant once it is implanted, securing the implant at the target site, explanting the implant, suturing tissue, etc.) a target position, site, or location of the implant (e.g., a location, orientation, etc.), and other aspects related to pre-operative, operative, or post-operative plans.

In some embodiments, the surgical plan includes an orthopedic surgical procedure such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). Spinal surgery can also include non-fusion surgeries, such as artificial disc replacements. In some embodiments, the surgical procedure includes descriptions of and/or instructions for performing one or more aspects of a patient-specific surgical procedure. For example, the surgical procedure can include one or more of a surgical approach, a corrective maneuver, or a bony resection.

In some embodiments, the surgical plan includes a target position of the implant. In some embodiments, the surgical plan optionally includes a recommendation to remove tissue to clear space for the implant at the target position. For example, the surgical plan may include instructions to perform an osteotomy, muscular resection, soft tissue detachment, soft tissue retraction, or the like to prepare the patient to receive the patient-specific implant. In some embodiments, the surgical plan includes a manipulation of tissue to prepare the patient to receive the implant. For example, the surgical plan may include instructions to adjust a relative position of two vertebrae, increase a distance between two vertebrae, or the like.

In some embodiments, the surgical plan includes machine-readable instructions for carrying out various steps of the surgical plan. The machine-readable instructions can be configured such that, when executed by a surgical robotic platform, the machine-readable instructions cause the surgical robotic platform to execute various aspects of an operative procedure associated with implanting the implant. For example, the surgical platform may prepare tissue for an incision, make an incision, make a resection, remove tissue, manipulate tissue, perform a corrective maneuver, deliver the implant to a target site, deploy the implant at the target site; adjust a configuration of the implant at the target site, manipulate the implant once it is implanted, secure the implant at the target site, explant the implant, suture tissue, and the like. The instructions may therefor include particular instructions for articulating robotic arms, instruments, and/or tools to perform or otherwise aid in the delivery of the patient-specific implant.

In some embodiments, the surgical plan includes step-by-step written, verbal, and/or graphic instructions that show a surgeon how to perform the patient-specific surgical plan. The patient-specific surgical plan can be displayed to the surgeon before and/or during the operative procedure (e.g., via display 822). In some embodiments, the written, verbal, and/or graphic instructions can be encoded in computer-readable instructions. The encoded instructions can be decoded and displayed to the surgeon before and/or during the operative procedure. In some embodiments, the patient-specific surgical plan includes both machine-readable instructions and written, verbal, and/or graphic illustrations.

In some embodiments, the system 800 may consider one or more reference data sets when designing the patient-specific implant and/or the patient-specific surgical plan. For example, in some embodiments the server 806 includes at least one database 820 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 820 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, preferences, and/or any other information or parameters relevant to the reference patient, such as any of the data described herein with respect to the patient data set 808. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 806 receives at least some of the reference patient data sets from a plurality of healthcare provider computing systems. Each healthcare provider computing system can include at least one reference patient data set (e.g., reference patient data sets) associated with reference patients treated by the corresponding healthcare provider. The reference patient data sets can include, for example, kinematic records, electronic medical records, electronic health records, biomedical data sets, etc.

In embodiments in which the implant and/or the surgical plan is designed based on the reference data, the data analysis module 816 can include one or more algorithms for identifying a subset of reference data from the database 820 that is likely to be useful in developing a treatment plan. For example, the data analysis module 816 can compare patient-specific data (e.g., the patient data set 808 received from the computing device 802) to the reference data from the database 820 (e.g., the reference patient data sets) to identify similar data (e.g., one or more similar patient data sets in the reference patient data sets). The comparison can be based on one or more parameters, such as age, gender, BMI, pathology, kinematics, lumbar lordosis, pelvic incidence, and/or treatment levels. The parameter(s) can be used to calculate a similarity score for each reference patient. The similarity score can represent a statistical correlation between the patient data set 808 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients. In some embodiments, the data analysis module 816 includes one or more algorithms that select a set or subset of the reference patient data based on criteria other than patient parameters, such as the surgical team data set 810 (e.g., based on surgeon expertise, outcomes of particular types of procedures performed by the surgeon, etc.) and/or the facility data set 812 (e.g., surgical equipment such as surgical robots).

The data analysis module 816 can further be configured with one or more algorithms to select a subset of the reference patient data sets, e.g., based on similarity to the patient data set 808 and/or treatment outcome of the corresponding reference patient. For example, the data analysis module 816 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, range of motion, kinematic data, HRQL, activity level, complications, recovery times, efficacy, mortality, or follow-up surgeries. As described in further detail below, in some embodiments, the data analysis module 816 calculates an outcome score by assigning values to each outcome parameter. A patient can be considered to have a favorable outcome if the outcome score is above, below, or at a specified threshold value.

In some embodiments, the data analysis module 816 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the health-care provider or physician can select the set of similarity and/or outcome parameters (or define new similarity and/or outcome parameters) used to generate the similarity and/or outcome score, respectively.

In some embodiments, the data analysis module 816 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of pro-cedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to varia-tion between diagnostic equipment. Additionally, patient-specific treatment plans can be developed for a particular health-care provider using data from similar healthcare providers (e.g., healthcare providers with traditionally simi-lar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgi-cal systems under similar conditions (e.g., size and capa-bilities of surgical teams, hospital resources, etc.).

In embodiments in which the implant and/or the surgical plan is designed based on the reference data, the treatment planning module 818 can include one or more algorithms that generate the implant and/or the surgical plan based on the reference data. In some embodiments, the treatment planning module 818 is configured to develop and/or imple-ment at least one predictive model for generating the treat-ment plan, also known as a "prescriptive model." The predictive model(s) can be developed using clinical knowl-edge, statistics, machine learning, AI, neural networks, or the like. In some embodiments, the output from the data analysis module 816 is analyzed (e.g., using statistics, machine learning, neural networks, AI, etc.) to identify correlations between data sets, patient parameters, health-care provider parameters, healthcare resource parameters, treatment procedures, medical device designs, and/or treat-ment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 818 is configured to generate the implant design based on previous treatment data from reference patients. For example, the treatment planning module 818 can receive a selected subset of reference patient data sets and/or similar patient data sets from the data analysis module 816, and determine or identify treatment data from the selected sub-set. The treatment data can include, for example, range of motion and/or other kinematic data, treatment procedure data (e.g., surgical procedure or intervention data) and/or medical device design data (e.g. implant design data) that are associated with favorable or desired treatment outcomes for the corresponding patient. The treatment planning mod-ule 818 can analyze the treatment procedure data and/or medical device design data to determine an optimal treat-ment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized treatment plan can be based on, at least in part, the patient-specific technologies or patient-specific selected technology.

Alternatively or in combination, the treatment planning module 818 can generate the implant designs based on correlations between data sets. For example, the treatment planning module 818 can correlate implant designs and medical device design data from implant designs for similar patients with favorable outcomes (e.g., as identified by the data analysis module 816). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 818 can generate designs using one or more AI techniques. AI techniques can be used to develop computing systems capable of simulating aspects of human intelli-gence, e.g., learning, reasoning, planning, problem solving, decision making, etc. AI techniques can include, but are not limited to, case-based reasoning, rule-based systems, artifi-cial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 818 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neu-ral networks) of the model. For example, the training data set can include any of the reference data stored in database 820, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vec-tors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate the treatment plan, the patient data set 808, the surgical team data set 810, and/or the facility data set 812 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 818 can use one or more of the machine learning models based the model's predicted accuracy score.

The implant design and/or the surgical plan generated by the treatment planning module 818 can be transmitted via the communication network 804 to the computing device 802 for output to a user (e.g., clinician, surgeon, healthcare provider, patient). In some embodiments, the computing device 802 includes or is operably coupled to a display 822. The display 822 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. Additionally or alternatively, the display 822 can show a design for the implant, such as a two- or three-dimensional model of the device design. The display 822 can also show patient information, such as two- or three-dimensional images or models of the patient's anatomy where the surgical procedure is to be performed and/or where the device is to be implanted. The display 822 can also display structural features of the implant suitable for contacting anatomical features to improve treatment, reduce implant movement, etc. The structural features can be rigid surfaces (e.g., outer surfaces of an implant body), anchors, fixation features, etc. Images of the implantation site can be analyzed to identify such anatomical features identified by the treatment planning module 818. The computing device 802 can further include one or more user input devices (not shown) allowing the user to modify, select, approve, and/or reject the displayed treatment plan(s).

In some embodiments, the patient-specific implant design generated by the treatment planning module 818 can be transmitted from the computing device 802 and/or the server 806 to a manufacturing system 824 for manufacturing a corresponding medical device. The manufacturing system 824 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 824 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 824 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 824 can manufacture one or more patient-specific medical devices based on fabrication instructions or data (e.g., CAD data, 3D data, digital blueprints, stereolithography data, or other data suitable for the various manufacturing technologies described herein). In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 818 generates control instructions configured to cause a surgical robot (e.g., robotic surgery systems, navigation systems, etc.) to partially or fully perform a surgical procedure. The control instructions can be transmitted to the robotic apparatus by the computing device 802 and/or the server 806.

Following the treatment of the patient in accordance with the treatment plan, treatment progress can be monitored over one or more time periods to update the data analysis module 816 and/or treatment planning module 818. Post-treatment data can be added to the reference data stored in the database 820. The post-treatment data can be used to train machine learning models for developing patient-specific treatment plans, patient-specific medical devices, or combinations thereof.

It shall be appreciated that the components of the system 800 can be configured in many different ways. For example, in alternative embodiments, the database 820, the data analysis module 816 and/or the treatment planning module 818 can be components of the computing device 802, rather than the server 806. As another example, the database 820, the data analysis module 816, and/or the treatment planning module 818 can be located across a plurality of different servers, computing systems, or other types of cloud-computing resources, rather than at a single server 806 or computing device 802.

Additionally, in some embodiments, the system 800 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like. In some embodiments, the system 800 may include additional features and/or capabilities, such as any of those described in U.S. application Ser. No. 16/735, 222, filed Jan. 6, 2020, the disclosure of which is incorporated by reference herein in its entirety.

FIG. 9 illustrates a computing device 900 suitable for use in connection with the system 800 of FIG. 8, according to an embodiment. The computing device 900 can be incorporated in various components of the system 800 of FIG. 8, such as the computing device 802 or the server 806. The computing device 900 includes one or more processors 910 (e.g., CPU(s), GPU(s), HPU(s), etc.). The processor(s) 910 can be a single processing unit or multiple processing units in a device or distributed across multiple devices. The processor(s) 910 can be coupled to other hardware devices, for example, with the use of a bus, such as a PCI bus or SCSI bus. The processor(s) 910 can be configured to execute one more computer-readable program instructions, such as program instructions to carry out of any of the methods described herein.

The computing device 900 can include one or more input devices 920 that provide input to the processor(s) 910, e.g., to notify it of actions from a user of the computing device 900. The actions can be mediated by a hardware controller that interprets the signals received from the input device and communicates the information to the processor(s) 910 using a communication protocol. Input device(s) 920 can include, for example, a mouse, a keyboard, a touchscreen, an infrared sensor, a touchpad, a wearable input device, a camera- or image-based input device, a microphone, or other user input devices.

The computing device 900 can include a display 930 used to display various types of output, such as text, models, virtual procedures, surgical plans, implants, graphics, and/or images (e.g., images with voxels indicating radiodensity units or Hounsfield units representing the density of the tissue at a location). In some embodiments, the display 930 provides graphical and textual visual feedback to a user. The processor(s) 910 can communicate with the display 930 via a hardware controller for devices. In some embodiments, the display 930 includes the input device(s) 920 as part of the display 930, such as when the input device(s) 920 include a touchscreen or is equipped with an eye direction monitoring system. In alternative embodiments, the display 930 is separate from the input device(s) 920. Examples of display devices include an LCD display screen, an LED display screen, a projected, holographic, or augmented reality display (e.g., a heads-up display device or a head-mounted device), and so on.

Optionally, other I/O devices 940 can also be coupled to the processor(s) 910, such as a network card, video card, audio card, USB, firewire or other external device, camera, printer, speakers, CD-ROM drive, DVD drive, disk drive, or Blu-Ray device. Other I/O devices 940 can also include input ports for information from directly connected medical equipment such as imaging apparatuses, including MRI machines, X-Ray machines, CT machines, etc. Other I/O devices 940 can further include input ports for receiving data from these types of machine from other sources, such as across a network or from previously captured data, for example, stored in a database.

In some embodiments, the computing device 900 also includes a communication device (not shown) capable of communicating wirelessly or wire-based with a network node. The communication device can communicate with another device or a server through a network using, for example, TCP/IP protocols. The computing device 900 can utilize the communication device to distribute operations across multiple network devices, including imaging equipment, manufacturing equipment, etc.

The computing device 900 can include memory 950, which can be in a single device or distributed across multiple devices. Memory 950 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 950 is a non-transitory computer-readable storage medium that stores, for example, programs, software, data, or the like. In some embodiments, memory 950 can include program memory 960 that stores programs and software, such as an operating system 962, one or more treatment assistance modules 964, and other application programs 966. The treatment assistance module(s) 964 can include one or more modules configured to perform the various methods described herein (e.g., the data analysis module 816 and/or treatment planning module 818 described with respect to FIG. 1). Memory 950 can also include data memory 970 that can include, e.g., reference data, configuration data, settings, user options or preferences, etc., which can be provided to the program memory 960 or any other element of the computing device 900.

FIG. 10 illustrates various aspects of an operative setup configured in accordance with the present technology. As shown, the operative setup can be used to implant a patient-specific artificial implant 1000 (which can be the same or generally similar to the implants described with respect to FIGS. 1A-5) into a patient P using a robotic surgical platform 1050 (hereinafter referred to as the "platform 1050"). The platform 1050 can be configured to perform or otherwise assist with one or more aspects of the operative procedure, including, for example, preparing tissue for an incision, making an incision, making a resection, removing tissue, manipulating tissue, performing a corrective maneuver, delivering the implant to a target site, deploying the implant at the target site, adjusting the implant at the target site, manipulating the implant once it is implanted, securing the implant at the target site, explanting the implant, suturing tissue, etc. For example, the platform 1050 can include one or more arms 1055 and end effectors for holding various surgical tools (e.g., graspers, clips, needles, needle drivers, irrigation tools, suction tools, staplers, screw driver assemblies, etc.), imaging instruments (e.g., cameras, sensors, etc.), and/or medical devices (e.g., the implant 1000) and that enable the platform 1050 to perform the one or more aspects of the surgical plan (e.g., positioning cages, forming mechanical connections, installing positioning features, implanting plates, etc.). Although shown as having one arm 1055, one skilled in the art will appreciate that the platform 1050 can have a plurality of arms (e.g., two, three, four, or more) and any number of joints, linkages, motors, and degrees of freedom. In some embodiments, the platform 1050 may have a first arm dedicated to holding one or more imaging instruments, while the remainder of the arms hold various surgical tools. In some embodiments, the tools can be releasably secured to the arms such that they can be selectively interchanged before, during, or after an operative procedure. The arms can be moveable through a variety of ranges of motion (e.g., degrees of freedom) to provide adequate dexterity for performing various aspects of the operative procedure.

The platform 1050 can include a control module 1060 for controlling operation of the arm(s) 1055. In some embodiments, the control module 1060 includes a user input device (not shown) for controlling operation of the arm(s) 1055. The user input device can be a joystick, a mouse, a keyboard, a touchscreen, an infrared sensor, a touchpad, a wearable input device, a camera- or image-based input device, a microphone, or other user input devices. A user (e.g., a surgeon) can interact with the user input device to control movement of the arm(s) 1055. In some embodiments, the control module 1060 includes one or more processors for executing machine-readable instructions that, when executed, automatically control operation of the arm 1055. In such embodiments, the control module 1060 may receive machine-readable instructions specifying one or more steps of a surgical procedure that, when executed by the control module 1060, cause the platform 1050 to perform the one or more steps of the surgical procedure. For example, the machine-readable instructions may direct the platform 1050 to prepare tissue for an incision, make an incision, make a resection, remove tissue, manipulate tissue, perform a corrective maneuver, deliver the implant 1000 to a target site, deploy the implant 1000 at the target site, adjust a configuration of the implant 1000 at the target site, manipulate the implant 1000 once it is implanted, secure the implant 1000 at the target site, explant the implant 1000, suture tissue, and the like. The instructions may therefor include particular instructions for articulating the arm 1055 to perform or otherwise aid in the delivery of the patient-specific implant.

If the surgical plan includes executable instructions, the platform 1050 can execute instructions to perform at least a portion of the surgical procedure. In some embodiments, the platform 1050 can generate executable instructions based on the surgical plan. For example, the surgical plan can include information about the delivery path, tools, and implantation site. The platform 1050 can analyze the surgical plan and develop executable instructions for performing the patient-specific procedure based on the capabilities (e.g., configuration and number of robotic arms, functionality of and effectors, guidance systems, visualization systems, etc.) of the robotic system. This enables the system 800 to be compatible with a wide range of different types of robotic surgery systems.

The platform 1050 can include one or more communication devices (e.g., components having VLC, WiMAX, LTE, WLAN, IR communication, PSTN, Radio waves, Bluetooth, and/or Wi-Fi operability) for establishing a connection with a network 1006 (which can be the same as the server 806 shown in FIG. 8) and/or a computing device 1040 (which can be the same as the computing device 902 shown in FIG. 9) for accessing and/or downloading the patient-specific plan. For example, the network 1006 can receive a request for a particular surgical plan from the platform 1050 and send the plan to the platform 1050. Once identified, the network 1006 can transmit the surgical plan directly to the platform 1050 for execution. In some embodiments, the network 1006 can transmit the surgical plan to one or more intermediate networked devices, rather than transmitting the surgical plan directly to the platform 1050. For example, the network 1006 may transmit the surgical plan to the computing device 1040 and/or the computing device 900, described previously with respect to FIG. 9. A user can review the surgical plan using the computing device before transmitting the surgical plan to the platform 1050 for execution. Additional details for identifying, storing, downloading, and accessing patient-specific surgical plans are described in U.S. application Ser. No. 16/990,810, filed Aug. 11, 2020, the disclosure of which is incorporated by reference herein in its entirety.

The platform 1050 can include additional components not expressly shown in FIG. 10. For example, in various embodiments the platform 1050 may include one or more displays (e.g., LCD display screen, an LED display screen, a projected, holographic, or augmented reality display (e.g., a heads-up display device or a head-mounted device), one or more I/O devices (e.g., a network card, video card, audio card, USB, firewire or other external device, camera, printer, speakers, CD-ROM drive, DVD drive, disk drive, or Blu-Ray device), and/or a memory (e.g., random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth). In some embodiments, the foregoing components can be generally similar to the like components described in detail with respect to computing device 900 in FIG. 9.

Without being bound by theory, using a robotic surgical platform to perform various aspects of the surgical plans described herein is expected to provide several advantages over conventional operative techniques. For example, use of robotic surgical platforms may improve surgical outcomes and/or shorten recovery times by, for example, decreasing incision size, decreasing blood loss, decreasing a length of time of the operative procedure, increasing the accuracy and precision of the surgery (e.g., the placement of the implant at the target location), and the like. The platform 1050 can also avoid or reduce user input errors, e.g., by including one or more scanners for obtaining information from instruments (e.g., instruments with retrieval features), tools, the patient specific implant 1000 (e.g., after the implant 1000 has been gripped by the arm 1055), etc. The platform 1050 can confirm use of proper instruments prior and during the surgical procedure. If the platform 1050 identifies an incorrect instrument or tool, an alert can be sent to a user that another instrument or tool should be installed. The user can scan the new instrument to confirm that the instrument is appropriate for the surgical plan. In some embodiments, the surgical plan includes instructions for use, a list of instruments, instrument specifications, replacement instruments, and the like. The platform 1050 can perform pre- and post-surgical checking routines based on information from the scanners.

<div align="center">CONCLUSION</div>

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHOPEDIC IMPLANT FIXATION;"

U.S. application Ser. No. 16/383,215, filed on Apr. 12, 2019, titled "SYSTEMS AND METHODS FOR ORTHOPEDIC IMPLANT FIXATION;"

U.S. application Ser. No. 16/569,494, filed on Sep. 12, 2019, titled "SYSTEMS AND METHODS FOR ORTHOPEDIC IMPLANTS;"

U.S. Application No. 62/773,127, filed on Nov. 29, 2018, titled "SYSTEMS AND METHODS FOR ORTHOPEDIC IMPLANTS;"

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS;"

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS;"

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;" and U.S. application Ser. No. 17/100,396, filed Nov. 20, 2020, titled "PATIENT-SPECIFIC VERTEBRAL IMPLANTS WITH POSITIONING FEATURES."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

We claim:

1. A computer-implemented method for designing a patient-specific lumbar implant assembly for a patient, the method comprising:

receiving, at a computer system, image data of a lumbar region of a spine of the patient;

generating, using the computer system, a virtual model of the lumbar region based at least in part on the image data;

manipulating, using the computer system, a spatial relationship between a first vertebra and a second vertebra within the virtual model of the lumbar region to reflect a planned surgical correction to the lumbar region;

measuring from the virtual model, using the computer system, a spinal metric of the lumbar region with the planned surgical correction, wherein the spinal metric includes one or more of a lumbar lordosis, a pelvic incidence, or a Cobb angle; and in response to the measured spinal metric complying with a predetermined criteria, designing, using the computer system, the patient-specific lumbar implant assembly to achieve the planned surgical correction when implanted in the lumbar region of the patient, wherein designing the patient-specific lumbar implant assembly includes— designing a patient-specific cage sized and shaped to be positioned at a first target position in an intervertebral space between the first vertebra and the second vertebra, the patient-specific cage having a first patient-specific topography designed to mate with contouring of the first vertebra and the second vertebra when seated at the first target position, and designing a patient-specific plate sized and shaped to be positioned at a second target position at which a first portion of the patient-specific plate engages an anterior or lateral surface of the first vertebra or the second vertebra, and a second portion of the patient-specific plate extends at least partially into the intervertebral space between the first vertebra and the second vertebra to engage the patient-specific cage, wherein the first portion has a second patient-specific topography designed to mate with contouring of the anterior or lateral surface of the first vertebra or the second vertebra, wherein the patient-specific implant assembly is configured such that placing the patient-specific plate at the second target position causes the second portion of the patient-specific plate to direct the patient-specific cage into the first target position.

2. The method of claim 1 wherein designing the patient-specific lumbar implant assembly includes:

designing the patient-specific cage to form a generally gapless interface with the first and second vertebra when the patient-specific plate is placed at the second target position, and designing the patient-specific plate to form a generally gapless interface with the anterior or lateral surface of the first or the second vertebra when the patient-specific plate is seated at the second target position.

3. The method of claim 1, further comprising automatically comparing, using the computer system, the measured spinal metric to the predetermined criteria, wherein the predetermined criteria includes a predetermined minimum value and/or a predetermined maximum value for the spinal metric.

4. The method of claim 3, further comprising:

in response to the measured spinal metric not complying with the predetermined criteria, further manipulating, using the computer system, the virtual model to redesign the planned surgical correction until the measured spinal metric complies with the predetermined criteria.

5. The method of claim 1, further comprising:

causing, using the computer system, the measured spinal metric and the virtual model to be stored on a remote server;

retrieving, using the computer system, the measured spinal metric and the virtual model;

further manipulating, using the computer system, the virtual model to display a revised planned surgical correction; and automatically redesigning, using the computer system, the patient-specific lumbar implant assembly to provide the revised planned surgical correction.

6. A computer-implemented method for designing a patient-specific implant assembly for a patient, the method comprising:

receiving, at a computer system, image data of a spinal region of a spine of the patient;

generating, using the computer system, a virtual model of the spinal region based at least in part on the image data;

manipulating, using the computer system, a spatial relationship between a first vertebra and a second vertebra within the virtual model of the spinal region to reflect a planned surgical correction to the spinal region;

measuring from the virtual model, using the computer system, a spinal metric of the spinal region with the planned surgical correction; and in response to the measured spinal metric complying with a predetermined criteria, designing, using the computer system, the patient-specific implant assembly to achieve the planned surgical correction when implanted in the spinal region of the patient, wherein designing the patient-specific implant assembly includes— designing a patient-specific cage sized and shaped to be positioned at a first target position in an intervertebral space between the first vertebra and the second vertebra, the patient-specific cage having a first patient-specific topography designed to mate with contouring of the first vertebra and the second vertebra when seated at the first target position, and designing a patient-specific plate sized and shaped to be positioned at a second target position at which a first portion of the patient-specific plate engages an anterior or lateral surface of the first vertebra or the second vertebra, and a second portion of the patient-specific plate extends at least partially into the intervertebral space between the first vertebra and the second vertebra to engage the patient-specific cage, wherein the first portion has a second patient-specific topography designed to mate with contouring of the anterior or lateral surface of the first vertebra or the second vertebra, wherein the patient-specific implant assembly is configured such that placing the patient-specific plate at the second target position causes the second portion of the patient-specific plate to direct the patient-specific cage into the first target position.

7. The method of claim 6 wherein designing the patient-specific implant assembly includes:

designing the patient-specific cage to form a generally gapless interface with the first and second vertebra when the patient-specific plate is placed at the second target position, and designing the patient-specific plate to form a generally gapless interface with the anterior or lateral surface of the first or the second vertebra when the patient-specific plate is seated at the second target position.

8. The method of claim 6, further comprising automatically comparing, using the computer system, the measured spinal metric to the predetermined criteria, wherein the predetermined criteria includes a predetermined minimum value and/or a predetermined maximum value for the spinal metric.

9. The method of claim 8, further comprising:

in response to the measured spinal metric not complying with the predetermined criteria, further manipulating, using the computer system, the virtual model to redesign the planned surgical correction until the measured spinal metric complies with the predetermined criteria.

10. The method of claim 6, further comprising:

causing, using the computer system, the measured spinal metric and the virtual model to be stored on a remote server;

retrieving, using the computer system, the measured spinal metric and the virtual model;

further manipulating, using the computer system, the virtual model to display a revised planned surgical correction; and automatically redesigning, using the computer system, the patient-specific implant assembly to provide the revised planned surgical correction.

11. The method of claim 6 wherein designing the patient-specific plate includes designing the second portion of the patient-specific plate to include a rigid interface between the patient-specific plate and the patient-specific cage.

12. The method of claim 11 wherein the rigid interface includes a screw, a bolt, a rivet, or a key-and-slot mechanism.

13. The method of claim 6 wherein the patient-specific implant assembly further includes a fastener configured to cause the patient-specific plate to engage with the patient-specific cage.

14. A computer-implemented method for designing a patient-specific implant assembly for a patient, the method comprising:

receiving, at a computer system, image data of a spine of the patient;

generating, using the computer system, a virtual model of the spine based at least in part on the image data;

manipulating, using the computer system, a spatial relationship between a first vertebra and a second vertebra within the virtual model of the spine to reflect a planned surgical correction to the spine; and designing, using the computer system, the patient-specific implant assembly to achieve the planned surgical correction when implanted in the spine of the patient, wherein designing the patient-specific implant assembly includes— designing a patient-specific cage sized and shaped to be positioned at a first target position in an intervertebral space between the first vertebra and the second vertebra, the patient-specific cage having a first patient-specific topography designed to mate with contouring of the first vertebra and the second vertebra when seated at the first target position, and designing a patient-specific plate sized and shaped to be positioned at a second target position at which a first portion of the patient-specific plate engages an anterior or lateral surface of the first vertebra or the second vertebra, and a second portion of the patient-specific plate extends at least partially into the intervertebral space between the first vertebra and the second vertebra to engage the patient-specific cage, wherein the first portion has a second patient-specific topography designed to mate with contouring of the anterior or lateral surface of the first vertebra or the second vertebra, wherein the patient-specific implant assembly is configured such that placing the patient-specific plate at the second target position causes the second portion of the patient-specific plate to direct the patient-specific cage into the first target position.

15. The method of claim 14 wherein designing the patient-specific implant assembly includes:

designing the patient-specific cage to form a generally gapless interface with the first and second vertebra when the patient-specific plate is placed at the second target position, and designing the patient-specific plate to form a generally gapless interface with the anterior or lateral surface of the first or the second vertebra when the patient-specific plate is seated at the second target position.

16. The method of claim 14 wherein designing the patient-specific plate includes designing the second portion of the patient-specific plate to include a rigid interface between the patient-specific plate and the patient-specific cage.

17. The method of claim 16 wherein the rigid interface includes a screw, a bolt, a rivet, or a key-and-slot mechanism.

18. The method of claim 14 wherein the patient-specific implant assembly further includes a fastener configured to cause the patient-specific plate to engage with the patient-specific cage.

19. The method of claim 14 wherein the patient is a particular patient, the method further comprising:

accessing a reference patient data set corresponding to one or more reference patients different from the particular patient, wherein the reference patient data set includes data representative of the one or more reference patients' anatomy and/or pathology, wherein the patient-specific implant assembly is designed based at least in part on the reference patient data set.

20. The method of claim 19, further comprising:

determining a similarity score between the one or more reference patients and the particular patient, wherein the similarity score is based on a comparison of the anatomy and/or pathology of the one or more reference patients with an anatomy and/or pathology of the particular patient; and selecting the one or more reference patients based on the similarity score meeting or exceeding a threshold similarity score.

* * * * *